United States Patent [19]
Henke et al.

[11] Patent Number: 5,648,333
[45] Date of Patent: Jul. 15, 1997

[54] PEPTIDES HAVING BRADYKININ ANTAGONIST ACTION

[75] Inventors: Stephan Henke, Hofheim am Taunus; Hiristo Anagnostopulos, Wiesbaden; Gerhard Breipohl, Frankfurt am Main; Jochen Knolle, Kriftel; Jens Stechl, Frankfurt am Main; Bernward Schölkens, Kelkeim/Taunus; Hans-Wolfram Fehlhaber, Idstein; Hermann Gerhards, Hofheim am Taunus; Franz Hock, Dieburg, all of Germany

[73] Assignee: Hoechst Aktiengesellschaft, Frankfurt am Main, Germany

[21] Appl. No.: 487,442

[22] Filed: Jun. 7, 1995

Related U.S. Application Data

[63] Continuation of Ser. No. 236,018, May 2, 1994, which is a continuation of Ser. No. 12,849, Feb. 3, 1993, abandoned, which is a continuation-in-part of Ser. No. 982,052, Nov. 25, 1992, abandoned, Ser. No. 837,090, Feb. 18, 1992, abandoned, and Ser. No. 969,523, Oct. 30, 1992, abandoned, which is a continuation of Ser. No. 841,766, Mar. 2, 1992, abandoned, which is a continuation of Ser. No. 690,297, Apr. 24, 1991, abandoned, which is a continuation-in-part of Ser. No. 565,270, Aug. 10, 1990, abandoned, which is a continuation-in-part of Ser. No. 374,162, Jun. 30, 1989, abandoned, said Ser. No. 982,052, is a continuation of Ser. No. 746,149, Aug. 14, 1991, abandoned, which is a continuation-in-part of Ser. No. 374,162, said Ser. No. 837,090, is a continuation-in-part of Ser. No. 565,270, and Ser. No. 746,149.

[30] Foreign Application Priority Data

| Nov. 24, 1988 | [DE] | Germany | 38 39 581.9 |
| May 19, 1989 | [DE] | Germany | 39 16 291.5 |
| Jun. 3, 1989 | [DE] | Germany | 39 26 225.8 |
| Aug. 14, 1989 | [DE] | Germany | 39 26 822.5 |
| Apr. 26, 1990 | [DE] | Germany | 40 13 270.6 |

[51] Int. Cl.$^6$ ............................. C07K 7/18; A61K 38/17
[52] U.S. Cl. .................. 514/2; 514/10; 514/15; 514/803; 530/314; 530/328
[58] Field of Search ................... 514/15, 10, 2, 514/803; 530/314, 328

[56] References Cited

U.S. PATENT DOCUMENTS

| 3,364,193 | 1/1968 | Hempel et al. | 514/14 |
| 4,242,329 | 12/1980 | Claeson et al. | 514/18 |
| 4,350,704 | 9/1982 | Hoefle et al. | 514/12 |
| 4,483,850 | 11/1984 | Patchett et al. | 424/177.1 |
| 4,515,803 | 5/1985 | Henning et al. | 514/338 |
| 4,693,993 | 9/1987 | Stewart et al. | 514/14 |
| 4,720,484 | 1/1988 | Vincent et al. | 514/18 |
| 4,801,613 | 1/1989 | Stewart et al. | 514/14 |
| 4,923,963 | 5/1990 | Stewart et al. | 514/14 |

FOREIGN PATENT DOCUMENTS

| 39431/89 | 5/1990 | Australia. |
| 612054 | 6/1991 | Australia. |
| 676/89 | 1/1990 | Chile. |
| 37294 | 5/1990 | Chile. |
| 0190058 | 8/1986 | European Pat. Off. . |
| 0370453 | 5/1990 | European Pat. Off. . |
| 219146 | 6/1990 | New Zealand. |
| WO86/07263 | 12/1986 | WIPO. |
| WO89/01781 | 3/1989 | WIPO. |

OTHER PUBLICATIONS

Eichler et al., eds., Handbook of Experimental Pharmacology, vol. 25, pp. 53–55 (1970).
Stewart, Handbook of Experimental Pharmacology, Erdos et al., ed. vol. 25, Supplement, pp. 227–272 (1979).
Morrison and Boyd, Organic Chemistry, 3rd ed., pp. 1018–1021 (1974).
Japan Kokai Tokko Koho, Chemical Abstract, 100: 138974K (1983), 8 pp. pp. 53–55 (1970).
Barabe et al., Canadian Journal of Physiology and Pharmacology, vol. 62, No. 6, pp. 627–629 (1984).
Vavrek et al., Peptides, vol. 6, pp. 161–164 (1985).
Vavrek et al., Peptides, vol. 9, pp. 655–658 (1985).
Vavrek et al., Chemical Abstracts, 105: 184127n (1986).
Regoli et al., Chemical Abstracts, 105: 36276v (1986).
Vavrek et al., Advances in Experimental Medicine and Biology, Part 198A, pp. 543–547 (1986).
Henke et al., Chemical Abstracts, 114: 207831q (1991).
Lyle et al., Journal of Medicinal Chemistry, vol. 34, No. 3, pp. 1230–1233 (1991).
Wirth et al., Br. J. Pharmacol., vol. 102, pp. 774–777 (1991).
Hock et al., Br. J. Pharmacol., vol. 102, pp. 768–774 (1991).

*Primary Examiner*—Cecilia J. Tsang
*Assistant Examiner*—P. Lynn Touzeau
*Attorney, Agent, or Firm*—Finnegan, Henderson, Farabow, Garrett & Dunner, L.L.P.

[57] ABSTRACT

Peptides of the formula I

A-B-C-E-F-K-P-G-M-F'-I      (I), wherein the terms A, B, C, E, F, K, P, G, M, F', and I are defined in the specification, have bradykinin antagonist action. Their therapeutic utility includes all pathological states which are mediated, caused or supported by bradykinin and bradykinin-related peptides.

33 Claims, No Drawings

PEPTIDES HAVING BRADYKININ ANTAGONIST ACTION

CROSS REFERENCE TO RELATED APPLICATIONS

This is a continuation of application Ser. No. 08/236,018, filed May 2, 1994; which is a continuation of application Ser. No. 08/012,849, filed Feb. 3, 1993, now abandoned; which is a continuation in part of application Ser. No. 07/982,052, filed Nov. 25, 1992 (now abandoned); which is a continuation of application Ser. No. 07/746,149, filed Aug. 14, 1991, now abandoned; which is a continuation in part of application Ser. No. 07/374,162, filed Jun. 30, 1989, now abandoned; said application Ser. No. 08/012,849, filed Feb. 3, 1993 (now abandoned) is a continuation in part of application Ser. No. 07/837,090, filed Feb. 18, 1992 (now abandoned); which is a continuation in part of application Ser. No. 07/565,270, filed Aug. 10, 1990 now abandoned and continuation in part of application Ser. No. 07/746,149, filed Aug. 14, 1991 now abandoned, said application Ser. No. 07/565,270, filed Aug. 10, 1990 (now abandoned) is a continuation in part of application Ser. No. 07/374,162, filed Jun. 30, 1989 now abandoned; said application Ser. No. 07/746,149, filed Aug. 14, 1991 now abandoned is a continuation in part of application Ser. No. 07/374,162, filed Jun. 30, 1989 now abandoned; said application Ser. No. 08/012,849, filed Feb. 13, 1993 now abandoned is a continuation in part of application Ser. No. 07/969,523, filed Oct. 30, 1992 (now abandoned); which is a continuation of application Ser. No. 07/841,766, filed Mar. 2, 1992 now abandoned; which is a continuation of application Ser. No. 07/690,297, filed Apr. 24, 1991 now abandoned; which is a continuation in part of application Ser. No. 07/565,270, filed Aug. 10, 1990 now abandoned; which is a continuation in part of Ser. No. 07/374,162, filed Jun. 30, 1989 now abandoned.

All of the above application Ser. Nos. 07/982,052; 07/746,149; 07/374,162; 07/837,090; 07/565,270; 07/969,523; 07/841,766; and 07/690,297, are specifically incorporated by reference for all of their disclosures and teachings.

SUMMARY AND DETAILED DESCRIPTION OF THE INVENTION

The present invention relates to novel peptides having bradykinin antagonist action and to a process for their preparation.

Bradykinin antagonist peptides are described in WO 86/07263 in which, inter alia, L-Pro in position 7 of the peptide hormone bradykinin or other bradykinin analogs is replaced by a D-amino acid, such as D-Phe, D-Thi, D-Pal, CDF, D-Nal, MDY, D-Phg, D-His, D-Trp, D-Tyr, D-hPhe, D-Val, D-Ala, D-His, D-Ile, D-Leu and DOMT.

The present invention is based on the object of finding novel active peptides having bradykinin antagonist action.

This object is achieved by the peptides of the formula I

A-B-C-E-F-K-P-G-M-F'-I   (I), in which

A $a_1$) denotes hydrogen,
  $(C_1-C_8)$-alkyl,
  $(C_1-C_8)$-alkanoyl,
  $(C_1-C_8)$-alkoxycarbonyl or
  $(C_1-C_8)$-alkylsulfonyl,
  in which in each case 1, 2 or 3 hydrogen atoms are optionally replaced by 1, 2 or 3 identical or different radicals from the series comprising
  carboxyl,
  amino,
  $(C_1-C_4)$-alkyl,
  $(C_1-C_4)$-alkylamino,
  hydroxyl,
  $(C_1-C_4)$-alkoxy,
  halogen,
  di-$(C_1-C_4)$-alkylamino,
  carbamoyl,
  sulfamoyl,
  $(C_1-C_4)$-alkoxycarbonyl,
  $(C_6-C_{12})$-aryl and
  $(C_6-C_{12})$-aryl-$(C_1-C_5)$-alkyl, or in which in each case 1 hydrogen atom is optionally replaced by a radical from the series comprising
    $(C_3-C_8)$-cycloalkyl,
    $(C_1-C_4)$-alkylsulfonyl,
    $(C_1-C_4)$-alkylsulfinyl,
    $(C_6-C_{12})$-aryl-$(C_1-C_4)$-alkylsulfonyl
    $(C_6-C_{12})$-aryl-$(C_1-C_4)$-alkylsulfinyl,
    $(C_6-C_{12})$-aryloxy,
    $(C_3-C_9)$-heteroaryl and
    $(C_3-C_9)$-heteroaryloxy and
    1 or 2 hydrogen atoms are replaced by 1 or 2 identical or different radicals from the series comprising
  carboxyl,
  amino,
  $(C_1-C_4)$-alkylamino,
  hydroxyl,
  $(C_1-C_4)$-alkoxy,
  halogen,
  di-$(C_1-C_4)$-alkylamino,
  carbamoyl,
  sulfamoyl,
  $(C_1-C_4)$-alkoxycarbonyl,
  $(C_6-C_{12})$-aryl and
  $(C_6-C_{12})$-aryl-$(C_1-C_5)$-alkyl, $a_2$) denotes
  $(C_3-C_8)$-cycloalkyl,
  carbamoyl, which may be optionally substituted on the nitrogen by $(C_1-C_6)$-alkyl or $(C_6-C_{12})$-aryl,
  $(C_6-C_{12})$-aryl,
  $(C_7-C_{18})$-aryloyl,
  $(C_6-C_{12})$-arylsulfonyl,
  $(C_3-C_9)$-heteroaryl, or $(C_3-C_9)$-heteroaryloyl,
  where in the radicals defined under $a_1$) and $a_2$) in each case aryl, heteroaryl, aryloyl, arylsulfonyl and heteroaryloyl is optionally substituted by 1, 2, 3 or 4 identical or different radicals from the series comprising
  carboxyl,
  amino,
  nitro,
  $(C_1-C_4)$-alkylamino,
  hydroxyl,
  $(C_1-C_4)$-alkyl,
  $(C_1-C_4)$-alkoxy,
  halogen,
  cyano,
  di-$(C_1-C_4)$-alkylamino,
  carbamoyl,
  sulfamoyl and
  $(C_1-C_4)$-alkoxycarbonyl, or $a_3$) denotes a radical of the formula II

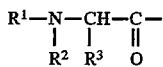

$R^1$ is defined as A under $a_1$) or $a_2$),
$R^2$ denotes hydrogen or methyl,
$R^3$ denotes hydrogen or $(C_1-C_6)$-alkyl, preferably $(C_1-C_4)$-alkyl, which is optionally monosubstituted by
amino,
substituted amino,
hydroxyl,
carboxyl,
carbamoyl,
guanidino,
substituted guanidino,
ureido,
mercapto,
methylmercapto,
phenyl,
4-chlorophenyl,
4-fluorophenyl,
4-nitrophenyl,
4-methoxyphenyl,
4-hydroxyphenyl,
phthalimido,
4-imidazolyl,
3-indolyl,
2-thienyl,
3-thienyl,
2-pyridyl,
3-pyridyl or
cyclohexyl,
where substituted amino stands for a compound —NH—A— and substituted guanidino stands for a compound —NH—C(NH)—NH—A, in which A is defined as under $a_1$) or $a_2$);

B stands for a basic amino acid in the L- or D-configuration, which may be substituted in the side chain;

C stands for a compound of the formula IIIa or IIIb

| G'-G'-Gly | G'-NH—$(CH_2)_n$—CO |
|---|---|
| (IIIa) | (IIIB) | in which
G' independently of one another denotes a radical of the formula IV

in which
$R^4$ and $R^5$ together with the atoms carrying them form a heterocyclic mono-, bi- or tricyclic ring system having 2 to 15 carbon atoms, and
n is 2 to 8;

E is a radical of an aromatic amino acid or is the residue of a neutral, acidic or basic aliphatic or alicyclic-aliphatic amino acid;

F independently of one another denotes the radical of a neutral, acidic or basic, aliphatic or aromatic amino acid which may be substituted in the side chain, or stands for a direct bond;

P denotes a radical of the formula V ((D)-Tic)

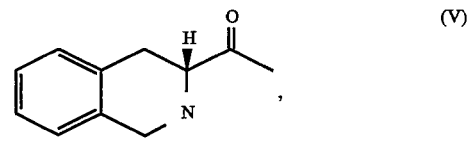

or D-phenylalanine ((D)-Phe) which may be optionally substituted in the phenyl moiety;

G is as defined above for G' or denotes a direct bond;

F' is as defined for F, denotes a radical —NH—$(CH_2)_n$—, with n=2 to 8, or, if G does not denote a direct bond, can stand for a direct bond, I is —OH, —$NH_2$ or —$NHC_2H_5$, K denotes the radical —NH—$(CH_2)_x$—CO— with x=1–4 or stands for a direct bond, and M is as defined for F, and their physiologically tolerable salts.

If not stated otherwise, the abbreviation of an amino acid radical without a stereodescriptor stands for the radical in the L-form (compare Schröder, Lübke, The Peptides, Volume I, New York 1965, pages XXII–XXIII; Houben-Weyl, Methoden der Organischen Chemie (Methods of Organic Chemistry), Volume XV/1 and 2, Stuttgart 1974), such as, for example, Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val.

When E is a radical of an aromatic amino acid and P is D-Tic, suitable radicals of a heterocyclic ring system of the formula IV are preferably radicals of heterocycles of the group below:

pyrrolidine (A);
piperidine (B);
tetrahydroisoquinoline (C);
decahydroisoquinoline (D);
octahydroindole (E);
octahydrocyclopenta[b]pyrrole (F);
2-aza-bicyclo[2.2.2]octane (G);
2-azabicyclo[2.2.1]heptane (H);
2-azaspiro[4.5]decane (I),
2-azaspiro[4.4]nonane (J);
spiro[(bicyclo[2.2.1]heptane)-2,3-pyrrolidine] (K);
spiro[(bicyclo[2.2.2]octane)-2,3-pyrrolidine] (L);
2-azatricyclo-[4.3.0.1$^{6,9}$]decane (M);
decahydrocyclohepta[b]pyrrole (N);
6octahydroisoindole (O);
octahydrocyclopenta[c]pyrrole (P);
2,3,3a,4,5,7a-hexahydroindole (Q);
tetrahydrothiazole (R);
2-azabicyclo[3.1.0]hexane (S);
isoxazolidine (T);
pyrazolidine (U); and
hydroxyproline (V);

all of which may be optionally substituted. These radicals are shown below:

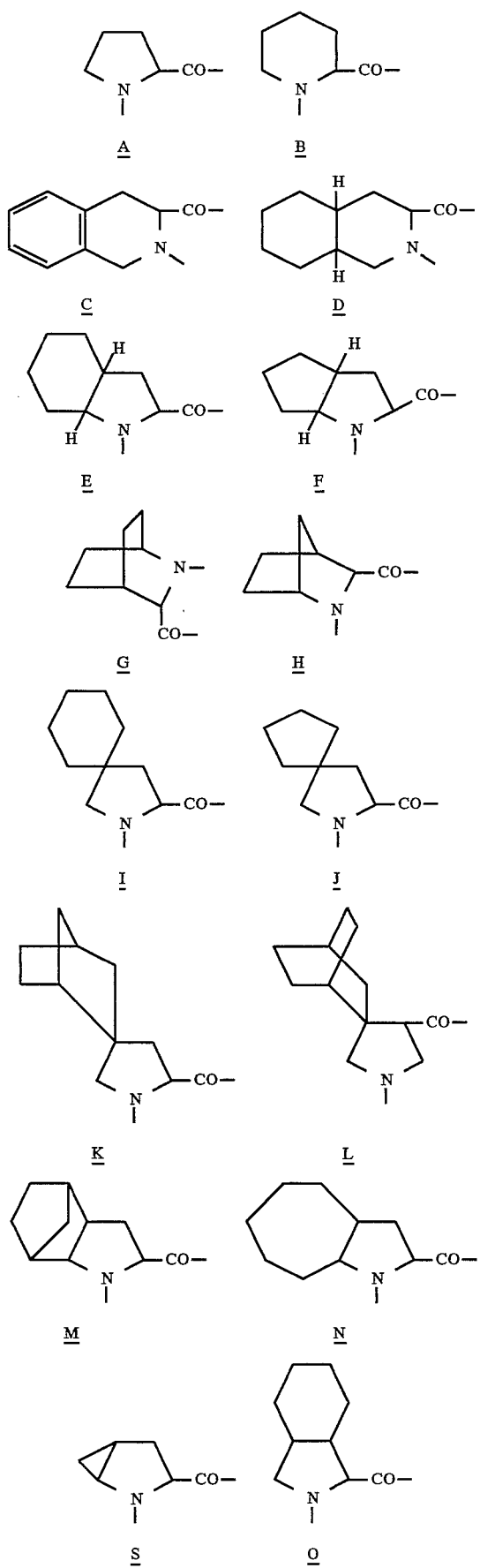

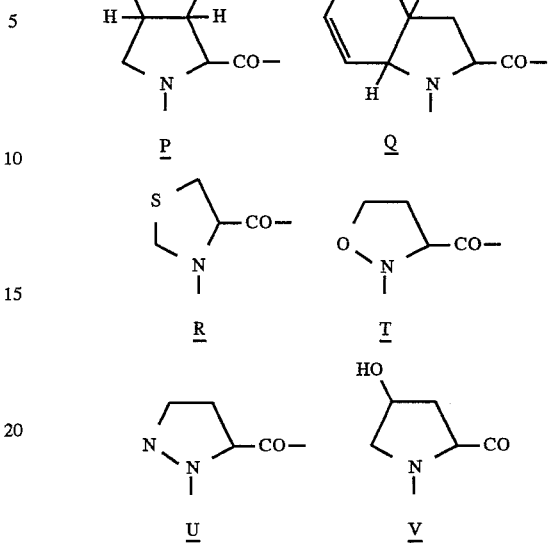

-continued

When (1) E is a radical of an aromatic amino acid and P is (D)-Phe, which is optionally substituted in the phenyl moiety or (2) E is the residue of a neutral, acidic or basic aliphatic or alicyclic-aliphatic amino acid and P is D-Tic, suitable radicals of a heterocyclic ring system of the formula IV are preferably radicals of heterocycles of the group below:

pyrrolidine-2-carboxylic acid;
piperidine-2-carboxylic acid;
1,2,3,4,-tetrahydroisoquinoline-3-carboxylic acid;
decahydroisoquinoline-3-carboxylic acid;
octahydroindole-2-carboxylic acid;
decahydroquinoline-2-carboxylic acid;
octahydrocyclopenta[b]pyrrole-2-carboxylic acid;
2-aza-bicyclo[2.2.2]octane-3-carboxylic acid;
2-azabicyclo[2.2.1]heptane-3-carboxylic acid;
2-azabicyclo[3.1.0]hexane-3-carboxylic acid;
2-azaspiro[4.4]nonane-3-carboxylic acid;
2-azaspiro[4.5]-decane-3-carboxylic acid;
spiro[(bicyclo[2.2.1]-heptane)-2,3-pyrrolidine-5-carboxylic acid];
spiro[(bicyclo[2.2.2]octane)-2,3-pyrrolidine-5-carboxylic acid];
2-azatricyclo[4.3.0.1$^{6,9}$]decane-3-carboxylic acid;
decahydrocyclohepta[b]pyrrole-2-carboxylic acid;
decahydrocycloocta[b]pyrrole-2-carboxylic acid;
octahydrocyclotenta[c]pyrrole-2-carboxylic acid;
octahydroisoindole-1-carboxylic acid;
2,3,3a,4,6a-hexahydrocyclopenta[b]pyrrole-2-carboxylic acid;
2,3,3a,4,5,7a-hexahydroindole-2-carboxylic acid;
tetrahydrothiazole-4-carboxylic acid;
isoxalidine-3-carboxylic acid;
pyrazolidine-3-carboxylic acid; and
hydroxyproline-2-carboxylic acid;

all of which may be optionally substituted. These radicals are shown below:

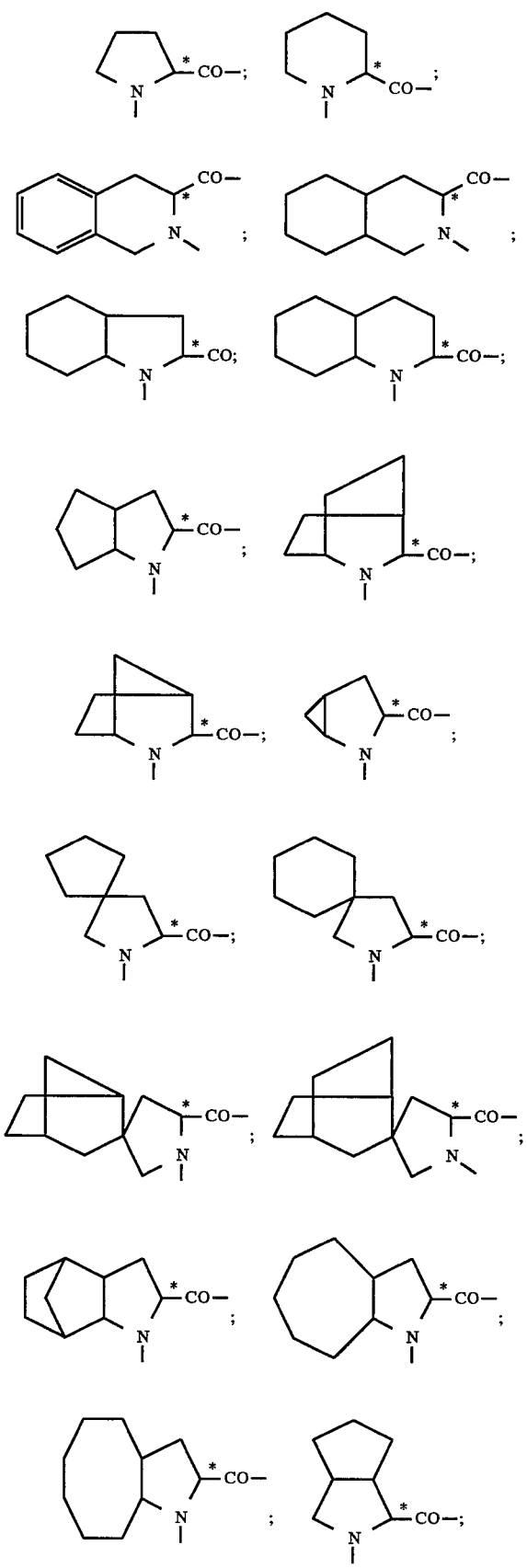

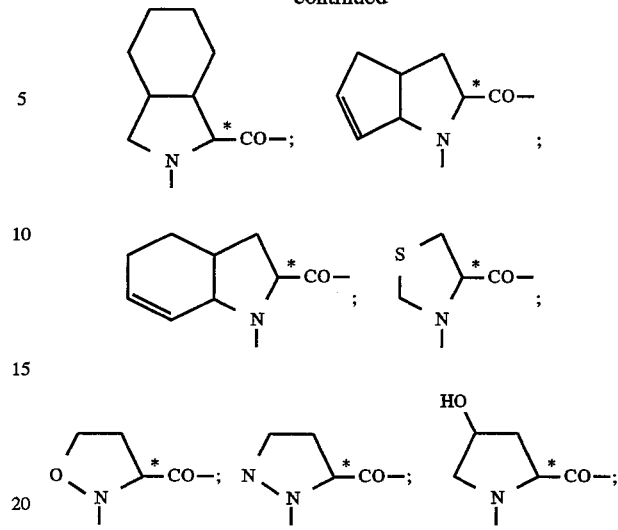

The heterocycles based on the above mentioned radicals are known, for example, from U.S. Pat. Nos. 4,344,949, 4,374,847, 4,350,704, EP-A-50,800, EP-A-31,741, EP-A-51,020, EP-A-49,658, EP-A-49,605, EP-A-29,488, EP-A-46,953, EP-A-52,870, EP-A-271,865, DE-A-3,226,768, DE-A-3,151,690, DE-A-3,210,496, DE-A-3,211,397, DE-A-3,211,676, DE-A-3,227,055, DE-A-3,242,151, DE-A-3,246,503 and DE-A-3,246,757.

Some of these heterocycles are furthermore proposed in DE-A-3,818,850.3.

If not stated otherwise in the individual case, alkyl can be straight chain or branched. The same applies to radicals derived therefrom, such as alkoxy, aralkyl or alkanoyl.

$(C_6-C_{12})$-Aryl preferably denotes phenyl, naphthyl or biphenylyl. Radicals derived therefrom, such as aryloxy, aralkyl or aroyl, are to be formulated correspondingly.

Halo stands for fluorine, chlorine, bromine or iodine, preferably for chlorine.

Preferred salts are alkali metal or alkaline earth metal salts, salts with physiologically tolerable amines and salts with inorganic or organic acids such as, for example, HCl, HBr, $H_2SO_4$, $H_3PO_4$, maleic acid, fumaric acid, citric acid, tartaric acid and acetic acid.

Preferred peptides of the formula I are those in which
1.
  E is a radical of an aromatic amino acid; and
  P is D-Tic;
2.
  E is a radical of an aromatic amino acid; and
  P is (D)-Phe which may be optionally substituted in the phenyl moiety; and
  E is the residue of a neutral, acidic or basic aliphatic or alicyclic-aliphatic amino acid; and
  P is D-Tic.

More preferred peptides of the formula I are those in which
1.
  B denotes Arg, Lys, Orn, 2,4-diaminobutyroyl or an L-homoarginine radical, where in each case the amino or guanidino group of the side chain may be substituted by as described under $a_1$) or $a_2$);
  E stands for the radical of an aromatic amino acid in the L- or D-configuration, which contains 6 to 14 carbon atoms in the aryl moiety as ring members, such as phenylalanine which is optionally substituted by halogen in the 2-, 3- or 4-position, tyrosine, O-methyltyrosine, 2-thienylalanine, 2-pyridylalanine or naphthylalanine;

P denotes D-Tic;

F' denotes the radical of a basic amino acid in the L- or D-configuration, such as Arg or Lys, where the guanidino —NH—$(CH_2)_n$— with n=2 to 8; and K group or amino group of the side chain may be replaced by A as described under $a_1$) or $a_2$), or denotes a radical K stands for the radical —NH—$(CH_2)_x$—CO— with x=2–4 or denotes a direct bond;

2.

B denotes Arg, Lys, Orn, 2,4-diaminobutyroyl or an L-homoarginine radical, where in each case the amino or guanidino group of the side chain may be substituted by A as described under $a_1$) or $a_2$);

E stands for the radical of an aromatic amino acid in the L- or D-configuration, which contains 6 to 14 carbon atoms in the aryl moiety as ring members, such as phenylalanine which is optionally substituted by halogen in the 2-, 3- or 4-position, tyrosine, O-methyltyrosine, 2-thienylalanine, 2-pyridylalanine or naphthylalanine;

P is D-Phe which may be optionally substituted in the phenyl moiety by halogen or $(C_1-C_4)$-alkoxy;

F' denotes the radical of a basic amino acid in the L- or D-configuration, such as Arg or Lys, where the guanidino group or amino group of the side chain may be replaced by A as described under $a_1$) or $a_2$), or denotes a radical —NH—$(CH_2)_n$— with n=2 to 8; and K stands for the radical —NH—$(CH_2)_x$—CO— with x=2–4 or denotes a direct bond; and

3.

B denotes Arg, Lys, Orn, 2,4-diaminobutyroyl or an L-homoarginine radical, where in each case the amino or guanidino group of the side chain may be substituted by A as described under $a_1$) or $a_2$);

E is the residue of an aliphatic or alicyclic-aliphatic amino acid which is in the L or D configuration and which contains 1 to 14 carbon atoms in the side chain, such as alanine, serine, threonine, O-$(C_1-C_6)$-alkyl- or O-$(C_6-C_{10})$-aryl-protected serine or threonine, valine, norvaline, leucine, isoleucine, norleucine, neopentylglycine, tert-butylglycine or $(C_3-C_7)$-cycloalkyl-$(C_1-C_3)$-alkylglycine;

P denotes D-Tic;

F' denotes the radical of a basic amino acid in the L- or D-configuration, such as Arg or Lys, where the guanidino group or amino group of the side chain may be replaced by A as described under $a_1$) or $a_2$), or denotes a radical —NH—$(CH_2)_n$— with n=2 to 8; and K stands for the radical —NH—$(CH_2)_x$—CO— with x=2–4 or denotes a direct bond.

Even more preferred peptides of the formula I are those in which

1.

B denotes Arg, Orn or Lys, where the guanidino group or the amino group of the side chain is unsubstituted or may be substituted by $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, where the aryl, heteroaryl, aryloyl, arylsulfonyl and heteroaryloyl radicals may optionally be substituted, as described under $a_2$), with 1, 2, 3 or 4 identical or different radicals;

E denotes phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine or β-(2-thienyl)alanine;

P denotes D-Tic;

K stands for a direct bond; and

M stands for a direct bond;

B denotes Arg, Orn or Lys, where the guanidino group or the amino group of the side chain is unsubstituted or may be substituted by $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, where the aryl, heteroaryl, aryloyl, arylsulfonyl and heteroaryloyl radicals may optionally be substituted, as described under $a_2$), with 1, 2, 3 or 4 identical or different radicals;

E denotes phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine or β-(2-thienyl)alanine;

P denotes D-Phe which may be optionally substituted by fluorine, chlorine, bromine or methoxy;

K stands for a direct bond; and

M stands for a direct bond; and

3.

B denotes Arg, Orn or Lys, where the guanidino group or the amino group of the side chain is unsubstituted or may be substituted by $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, where the aryl, heteroaryl, aryloyl, arylsulfonyl and heteroaryloyl radicals may optionally be substituted, as described under $a_2$), with 1, 2, 3 or 4 identical or different radicals.

E denotes leucine, isoleucine, norleucine, tert-butylglycine, serine, threonine or cyclohexylalanine;

P denotes D-Tic;

K stands for a direct bond; and

M stands for a direct bond.

Still even more preferred peptides of the formula I are those in which

1.

A denotes hydrogen, (D)- or (L)-H-Arg, (D)- or (L)-H-Lys or (D)- or (L)-H-Orn;

B denotes Arg, Orn or Lys, where the guanidino group or the amino group of the side chain may be substituted by hydrogen, $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, where the aryl, heteroaryl, aryloyl, arylsulfonyl and heteroaryloyl radicals may optionally be substituted with 1, 2, 3 or 4 identical or different radicals from the series comprising methyl, methoxy and halogen;

C denotes Pro-Pro-Gly, Hyp-Pro-Gly or Pro-Hyp-Gly;

E denotes Phe or Thia;

F denotes Ser, hSer, Lys, Leu, Val, Nle, Ile or Thr;

P denotes D-Tic;

K stands for a direct bond;

M stands for a direct bond;

G stands for the radical of a heterocyclic ring system of the formula IV, where the radicals of the heterocycles pyrrolidine (A); piperidine (B); tetrahydroisoquinoline (C); cis- and trans-decahydroisoquinoline (D); cis-endo-octahydroindole (E), cis-exo-octahydroindole (E), trans-octahydroindole (E), cis-endo-, cis-exo-, trans-octahydrocyclopentano[b]pyrrole (F), or hydroxyproline (V) are preferred;

F' denotes Arg; and

I stands for OH;

2.

A denotes hydrogen, (D)- or (L)-H-Arg, (D)- or (L)-H-Lys or (D)- or (L)-H-Orn;

B denotes Arg, Orn or Lys, where the guanidino group or the amino group of the side chain may be substituted by hydrogen, $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, where the aryl, heteroaryl, aryloyl, arylsulfonyl and heteroaryloyl radicals may optionally be substituted with 1, 2, 3 or 4 identical or different radicals from the series comprising methyl, methoxy and halogen;

C denotes Pro-Pro-Gly, Hyp-Pro-Gly or Pro-Hyp-Gly;

E denotes Phe or Thia;

F denotes Ser, hSer, Lys, Leu, Val, Nle, Ile or Thr;

P denotes (D)-Phe which may be optionally substituted in the phenyl moiety;

K stands for a direct bond;

M stands for a direct bond;

G stands for the radical of a heterocyclic ring system of the formula IV, where the radicals of the heterocycles pyrrolidine-2-carboxylic acid; piperidine-2-carboxylic acid; 1,2,3,4-tetrahydroisoquinoline-3-carboxylic acid, cis- and trans-decahydroisoquinoline-3-carboxylic acid; cis-endo-,cis-exo-,trans-octahydroindole-2-carboxylic acid, cis-endo-, cis-exo-, trans-octahydrocyclopentano[b]pyrrole-2-carboxylic acid or hydroxyproline-2-carboxylic acid are preferred;

F' denotes Arg; and

I stands for OH; and

A denotes hydrogen, (D)- or (L)-H-Arg, (D)- or (L)-H-Lys or (D)- or (L)-H-Orn;

B denotes Arg, Orn or Lys, where the guanidino group or the amino group of the side chain may be substituted by hydrogen, $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, where the aryl, heteroaryl, aryloyl, arylsulfonyl and heteroaryloyl radicals may optionally be substituted with 1, 2, 3 or 4 identical or different radicals from the series comprising methyl, methoxy and halogen;

C denotes Pro-Pro-Gly, Hyp-Pro-Gly or Pro-Hyp-Gly;

E denotes Leu, Ile, Tbg or Cha;

F denotes Ser, hSer, Lys, Leu, Val, Nle, Ile or Thr;

P denotes D-Tic;

K stands for a direct bond;

M stands for a direct bond;

G stands for the radical of a heterocyclic ring system of the formula IV, where the radicals of the heterocycles pyrrolidine-2-carboxylic acid; piperidine-2-carboxylic acid; 1,2,3,4-tetrahydroisoquinoline-3-carboxylic acid, cis- and trans-decahydroisoquinoline-3-carboxylic acid; cis-endo-,cis-exo-,trans-octahydroindole-2-carboxylic acid, cis-endo-, cis-exo-, trans-octahydrocyclopentano[b]pyrrole-2-carboxylic acid or hydroxyproline-2-carboxylic acid are preferred;

F' denotes Arg; and

I stands for OH.

Examples of very particularly preferred peptides of the formula I are:

H-D-Arg-Arg-Hyp-Pro-Gly-Phe-Ser-D-Tic-Oic-Arg-OH;
H-D-Arg-Arg-Pro-Pro-Gly-Phe-Ser-D-Tic-Oic-Arg-OH;
H-D-Arg-Arg-Hyp-Pro-Gly-Thia-Ser-D-Tic-Aoc-Arg-OH;
H-D-Arg-Arg-Pro-Hyp-Gly-Thia-Ser-D-Tic-Aoc-Arg-OH;
H-D-Arg-Arg-Pro-Hyp-Gly-Thia-Ser-D-Tic-Tic-Arg-OH;
H-D-Arg-Arg-Pro-Hyp-Gly-Thia-Ser-D-Tic-Oic-Arg-OH;
H-D-Arg-Arg-Pro-Pro-Gly-Thia-Ser-D-Tic-Oic -Arg-OH;
H-D-Arg-Arg-Pro-Hyp-Gly-Phe-Ser-D-Tic-Oic-Arg-OH;
H-D-Arg-Arg(NO$_2$ )-Pro-Hyp-Gly-Phe-Ser-D-Tic-Aoc-Arg-OH;
H-Arg(Tos)-Pro-Hyp-Gly-Thia-Ser-D-Tic-Oic-Arg-OH;
H-(D)-Arg-Arg-Pro-Hyp-Gly-Phe-Ser-(D)-Phe-Oic-Arg-OH;
H-(D)-Arg-Arg-Pro-Hyp-Gly-Thia-Ser-(D)-Phe-Oic-Arg-OH;
H-(D)-Arg-Arg-Pro-Pro-Gly-Phe-Ser-(D)-(p-Cl)Phe-Oic-Arg-OH;
H-(D)-Arg-Arg-Pro-Hyp-Gly-Leu-Ser-(D)-Tic-Oic-Arg-OH;
H-(D)-Arg-Arg-Pro-Hyp-Gly-Cha-Ser-(D)-Tic-Oic-Arg-OH; or
H-(D)-Arg-Arg-Pro-Hyp-Gly-Tbg-Ser-(D)-Tic-Oic-Arg-OH.

The most preferred peptide of the formula I is H-D-Arg-Arg-Pro-Hyp-Gly-Thia-Ser-D-Tic-Oic-Arg-OH.

The invention furthermore relates to a process for the preparation of peptides of the formula I, which comprises a) reacting a fragment having a C-terminal free carboxyl group or its activated derivative with an appropriate fragment having an N-terminal free amino group or b) synthesizing the peptide stepwise, optionally splitting off one or more protective groups temporarily introduced for the protection of other functions in the compound obtained according to (a) or (b) and optionally converting the compounds of the formula I thus obtained into their physiologically tolerable salt.

The peptides of the present invention were prepared by generally known methods of peptide chemistry, see, for example, Houben-Weyl, Methoden der organischen Chemie (Methods of Organic Chemistry), Volume 15/2, and preferably by means of solid phase synthesis such as described, for example, by B. Merrifield, J. Am. Chem. Soc. 85, 2149 (1963) or R. C. Sheppard, Int. J. Peptide Protein Res. 21, 118 (1983) or by equivalent known methods. Urethane protective groups such as, for example, the tert-butyloxy-carbonyl (Boc) or fluorenylmethoxycarbonyl (Fmoc) protective group are used as α-amino protective group. If necessary for the prevention of side reactions or for the synthesis of specific peptides, the functional groups in the side chain of amino acids are additionally protected by suitable protective groups (see, for example, T. W. Greene, "Protective Groups in Organic Synthesis"), where primarily, Arg(Tos), Arg(Mts), Arg(Mtr), Arg(PMC), Asp(OBzl), Asp(OBut), Cys(4-MeBzl), Cys(Acm), Cys(SBut), Glu(OBzl), Glu(OBut), His (Tos), His(Fmoc), His(Dnp), His(Trt), Lys(Cl-Z), Lys(Boc), Met(O), Ser(Bzl), Ser(But), Thr(Bzl), Thr(But), Trp(Mts), Trp(CHO), Tyr(Br-Z), Tyr(Bzl) or Tyr(But) are employed.

Solid phase synthesis begins at the C-terminal end of the peptide with the coupling of a protected amino acid to an appropriate resin. Starting materials of this type may be obtained by linking a protected amino acid via an ester or amide bond to a polystyrene or polyacrylamide resin modified with a chloromethyl, hydroxymethyl, benzhydryl-amino (BHA) or methylbenzhydrylamino (MBHA) group. The resins used as support materials are commercially obtainable. BHA and MBHA resins are usually used if the peptide synthesized is intended to have a free amide group at the C-terminus. If the peptide is intended to have a secondary amide group at the C-terminal end, a chloromethyl or hydroxymethyl resin is used and the splitting off is carried out using the corresponding amines. If it is wished to obtain, for example, the ethylamide, the peptide can be split off from the resin using ethylamine, the splitting off of the side chain protective groups subsequently being carried out by means of other suitable reagents. If it is intended to retain the tert-butyl protective groups of the amino acid side chain in the peptide, the synthesis is carried out using the Fmoc protective group for temporary blocking of the α-amino group of the amino acid using the method described, for example, in R. C. Sheppard, J. Chem. Soc., Chem. Comm 1982, 587, the guanidino function of the arginine being protected by protonation with pyridinium perchlorate and the protection of the other functionalized amino acids in the side chain being carried out using benzyl protective groups which can be split off by means of catalytic transfer hydrogenation (A. Felix et al., J. Org. Chem. 13, 4194 (1978)) or by means of sodium in liquid ammonia (W. Roberts, J. Am. Chem. Soc. 76, 6203 (1954)).

After splitting off the amino protective group of the amino acid coupled to the resin using a suitable reagent, such as, for example, trifluoroacetic acid in methylene chloride in the case of the Boc protective group or a 20% strength solution of piperidine in dimethylformamide in the case of the Fmoc protective group, the subsequently protected amino acids are successively coupled in the desired sequence. The intermediately resulting N-terminal protected peptide resins are deblocked by means of the reagents described above before linkage with the subsequent amino acid derivative.

All possible activating reagents used in peptide synthesis can be used as coupling reagents, see, for example, Houben-Weyl, Methoden der organischen Chemie (Methods of Organic Chemistry), Volume 15/2, in particular, however, carbodiimides such as, example, N,N'-dicyclohexylcarbodiimide, N,N'-diisopropylcarbodiimide or N-ethyl-N'-(3-dimethylaminopropyl)-carbodiimide. The coupling can in this case be carried out directly by addition of amino acid derivative and the activating reagent and, if desired, a racemization-suppressing additive such as, for example, 1-hydroxy-benzotriazole (HOBt) (W. König, R. Geiger, Chem. Ber. 103, 708 (1970)) or 3-hydroxy-4-oxo-3,4-dihydrobenzo-triazine (HOObt) (W. König, R. Geiger, Chem. Ber. 193, 2054 (1970)) to the resin or, however, the preactivation of the amino acid derivative as symmetrical anhydride or HOBt or HOObt ester can be carried out separately and the solution of the activated species in a suitable solvent can be added to the peptide resin capable of coupling.

The coupling or activation of the amino acid derivative with one of the above mentioned activating reagents can be carried out in dimethylformamide, N-methylpyrrolidone or methylene chloride or a mixture of the solvents mentioned. The activated amino acid derivative is customarily employed in a 1.5 to 4 fold excess. In cases in which an incomplete coupling takes place, the coupling reaction is repeated without previously carrying out the deblocking of the α-amino group of the peptide resin necessary for the coupling of the following amino acid.

The successful course of the coupling reaction can be monitored by means of the ninhydrin reaction, such as described, for example, by E. Kaiser et al., Anal. Biochem. 34, 595 (1970). The synthesis can also be automated, for example using a peptide synthesizer model 430A from Applied Biosystems, it being possible either to use the synthesis program provided by the apparatus manufacturer or else, however, one set up by the user himself. The latter are in particular employed in the use of amino acid derivatives protected with the Fmoc group.

After synthesis of the peptides in the previously described manner, the peptide can be split off from the resin using reagents, such as, for example, liquid hydrogen fluoride (preferably in the peptides prepared according to the Boc method) or trifluoroacetic acid (preferably in the peptides synthesized according to the Fmoc method). These reagents not only cleave the peptide from the resin but also the other side chain protective groups of the amino acid derivative. In this manner, the peptide is obtained in the form of the free acid in addition using BHA and MBHA resins. With the BHA or MBHA resins, the peptide is obtained as acid amide when splitting off is carried out using hydrogen fluoride or trifluoromethanesulfonic acid. Additional processes for the preparation of peptide amides are described in German Patent Application Nos. P 37 11 866.8 and P 37 43 620.1 and Europe Patent Applications Nos. 271,865, 287,882 and 322,348. The splitting off of the peptide amides from the resin here is carried out by treatment with medium strength acids (for example trifluoroacetic acid) usually used in peptide synthesis, cation entrainer substances such as phenol, cresol, thiocresol, anisole, thioanisole, ethanedithiol, dimethyl sulfide, ethyl methyl sulfide or similar cation entrainers customary in solid phase synthesis being added individually or as a mixture of two or more of these auxiliaries. In this case, the trifluoroacetic acid can also be used diluted by suitable solvents, such as, for example, methylene chloride.

If the tert-butyl or benzyl side chain protective groups of the peptides are to be retained, the splitting off of the peptide synthesized on a particularly modified support resin is carried out using 1% trifluoroacetic acid in methylene chloride, such as described, for example, in R. C. Sheppard, J. Chem. Soc., Chem. Comm. 1982, 587. If individual tert-butyl or benzyl side chain protective groups are to be retained, a suitable combination of synthesis and splitting off methods is used.

For the synthesis of peptides having a C-terminal amide grouping or an ω-amino or ω-guanidinoalkyl grouping, the modified support resin described by Sheppard is likewise used. After the synthesis, the peptide fully protected in the side chain is split off from the resin and subsequently reacted with the appropriate amine or ω-aminoalkylamine or ω-guanidinoalkylamine in classical solution synthesis, it being possible for optionally present additional functional groups to be temporarily protected in a known manner.

An additional process for the preparation of peptides having an ω-aminoalkyl grouping is described in German Patent Application P 36 35 670.0 and European Patent Application 264,802.

The peptides of the present invention were preferably synthesized by two general protective group tactics using the solid phase technique:

The synthesis was carried out using an automatic peptide synthesizer model 430 A from Applied Biosystems, with Boc or Fmoc protective groups for temporary blockage of the α-amino group.

When using the Boc protective group, the synthesis cycles pre-programmed by the manufacturer of the apparatus were used for the synthesis.

The synthesis of the peptides having a free carboxyl group on the C-terminal end was carried out on a 4-(hydroxymethyl)phenylacetamidomethylpolystyrene resin functionalized with the corresponding Boc amino acid (R. B. Merrifield, J. Org. Chem. 43, 2845 (1978)) from Applied Biosystems. An MBHA resin from the same firm was used for the preparation of the peptide amides. N,N'-dicyclohexylcarbodiimide or N,N'-diisopropylcarbodiimide were used as activating reagents. Activation was carried out as the symmetrical anhydride, as the HOBt ester or HOObt ester in $CH_2Cl_2$, $CH_2Cl_2$-DMF mixtures or NMP. 2–4 equivalents of activated amino acid derivative were employed for the coupling. In cases in which the coupling took place incompletely, the reaction was repeated.

During the use of the Fmoc protective group for the temporary protection of the α-amimo group, our own synthesis programs were used for synthesis using the automatic peptide synthesizer model 430A from Applied Biosystems. The synthesis was carried out on a p-benzyloxybenzyl alcohol resin (S. Wang, J. Am. Chem. Soc. 95, 1328 (1973)) from Bachem which was esterified by a known method (E. Atherton et al., J.C.S. Chem. Comm. 1981, 336) using the appropriate amino acid. The activation of the amino acid derivatives as HOBt or HOObt esters was carried out directly in the amino acid cartridges provided by the apparatus manufacturer by addition of a solution of diisopropylcarbodiimide in previously weighed-in mixture of amino acid derivative and HOBt or HOObt. Fmoc-amino acid-OObt esters prepared in substance can likewise be employed as described in European Patent Application No. 247,573. The splitting off of the Fmoc protective group was carried out using a 20% strength solution of piperidine in DMF in the reaction vessel. The excess of reactive amino acid derivative used was 1.5 to 2.5 equivalents. If the coupling was not complete, it was repeated as in the Boc method.

The peptides according to the invention have, individually or in combination, a bradykinin antagonist action which can be tested in various models (see Handbook of Exp. Pharmacol. Vol. 25, Springer Verlag, 1970, p. 53–55), for example on the isolated rat uterus, on the guinea pig ileum or on the isolated pulmonary artery of the guinea pig.

For testing the peptides according to the invention on the isolated arteria pulmonalis, guinea pigs (Dunkin Hartley) having a weight of 400–450 g are sacrificed by a blow to the back of the neck.

The thorax is opened and the arteria pulmonalis is carefully dissected out. The surrounding tissue is carefully removed and the arteria pulmonalis is cut spirally at an angle of 45°.

The vessel strip of 2.5 cm length and 3–4 mm width is fixed in a 10 ml capacity organ bath which is filled with Ringer solution.

| Composition of the solution in mmol/l | |
|---|---|
| NaCl | 154 |
| KCl | 5.6 |
| $CaCl_2$ | 1.9 |
| $NaHCO_3$ | 2.4 |
| Glucose | 5.0 |

95% $O_2$ and 5% $CO_2$ is bubbled through the solution, which is warmed to 37° C. The pH is 7.4 and the preload on the vessel strip is 1.0 g.

The isotonic contraction changes are detected using a lever arrangement and an HF modem (position sensor) from Hugo Sachs and recorded on a compensating recorder (BEC, Goerz Metrawatt SE 460).

After equilibration for 1 hour, the experiment is begun. After the vessel strips have achieved their maximum sensitivity to $2\times10^{-7}$ mol/l of bradykinin—bradykinin leads to a contraction of the vessel strips—the peptides are allowed to act for 10 minutes in each case in the doses $5\times10^{-8}$–$1\times10^{-5}$ mol/l and, after adding bradykinin again, the decrease in the effect of bradykinin as opposed to the control is compared.

For the detection of a partial agonistic effect, the peptides are used in the doses $1\times10^{-5}$–$1\times10^{-3}$ mol/l.

The $IC_{50}$ values of some of the peptides according to the invention calculated from the dose-effect curves are shown in Table 1.

TABLE 1

| Compound | $IC_{50}$ [M] |
|---|---|
| H-(D)-Arg—Arg—Hyp—Pro—Gly—Phe—Ser-(D)-Tic—Phe—Arg—OH | $4.6 \times 10^{-6}$ |
| H-(D)-Arg—Arg—Hyp—Pro—Gly—Thia—Ser-(D)-Tic—Thia—Arg—OH | $2.1 \times 10^{-6}$ |
| H-(D)-Arg—Arg—Pro—Hyp—Gly—Phe—Ser-(D)-Tic—Phe—Arg—OH | $1.2 \times 10^{-5}$ |
| H-(D)-Arg—Arg—Hyp—Pro—Gly—Phe—Gly-(D)-Tic—Phe—Arg—OH | $2.4 \times 10^{-5}$ |
| H-(D)-Arg—Arg—Pro—Hyp—Gly—Phe—Ser-(D)-Tic—Phe—Arg(Mtr)—OH | $2.5 \times 10^{-5}$ |
| H-(D)-Arg—Arg—Hyp—Pro—Gly—Phe—Ser-(D)-Tic—Pro—Arg—OH | $2.5 \times 10^{-7}$ |
| H-(D)-Arg—Arg—Hyp—Pro—Gly—Thia—Ser-(D)-Tic—Pro—Arg—OH | $1.9 \times 10^{-7}$ |
| H-(D)-Arg—Arg—Hyp—Pro—Gly—Thia—Ser-(D)-Tic—Aoc—Arg—CH | $5.6 \times 10^{-8}$ |
| H-(D)-Arg—Arg—Hyp—Pro—Gly—Thia—Ser—β—Ala-(D)-Tic—Aoc—Arg—OH | $1.7 \times 10^{-6}$ |
| H-(D)-Arg—Arg—Hyp—Pro—Gly—Thia—Ser—Gly-(D)-Tic—Aoc—Arg—OH | $3.9 \times 10^{-7}$ |
| H-(D)-Arg—Arg—Hyp—Pro—Gly—Thia—Gly-(D)-Tic-(D,L)-Oic—Arg—OH | $3.2 \times 10^{-7}$ |
| H-(D)-Arg-(D)-Arg—Hyp—Pro—Gly—Thia—Ser-(D)-Tic—Aoc—Arg—OH | $4.8 \times 10^{-7}$ |
| H-(D)-Arg—Arg—Hyp—Pro—Gly—Thia—Ser-(D)-Tic—Tic—Arg—OH | $1.7 \times 10^{-7}$ |
| H-(D)-Arg—Arg—Pro—Hyp—Gly—Thia—Ser-(D)-Tic—Aoc—A—rg—OH | $1.1 \times 10^{-8}$ |
| H-(D)-Arg—Arg—Pro—Hyp—Gly—Phe—Ser-(D)-Tic—Aoc—Arg—OH | $4.6 \times 10^{-8}$ |
| H-(D)-Tyr—Arg—Pro—Hyp—Gly—Thia—Ser-(D)-Tic—Aoc—Arg—OH | $6.2 \times 10^{-8}$ |
| H-(D)-Arg—Arg—Pro—Hyp—Gly—Thia—Ser-(D)-Tic-(D)-Oic—Arg—OH | $2.6 \times 10^{-5}$ |
| H-(D)-Arg—Arg—Pro—Hyp—Gly—Thia—Ser-(D)-Tic—Oic—Arg—OH | $5.4 \times 10^{-9}$ |
| H-(D)-Arg—Lys—Pro—Hyp—Gly—Phe—Ser-(D)-Tic—Aoc—Arg—CH | $3.2 \times 10^{-7}$ |
| H-(D)-Arg—Arg—Pro—Hyp—Gly—Phe—Ser-(D)-Tic—Oic—Arg—OH | $6.8 \times 10^{-9}$ |
| H-(D)-Arg—Arg(NO$_2$)—Pro—Hyp—Gly—Phe—Ser-(D)-Tic—Aoc—Arg—OH | $6.4 \times 10^{-8}$ |
| H-(D)-Arg—Arg—Pro—Pro—Gly—Thia—Ser-(D)-Tic—Oic—Arg—OH | $4.2 \times 10^{-9}$ |
| H-(D)-Arg—Pro—Hyp—Gly—Phe—Ser-(D)-Tic—Oic—Arg—OH | $3.4 \times 10^{-7}$ |
| H—Arg(Tos)—Pro—Hyp—Gly—Phe—Ser-(D)-Tic—Oic—Arg—OH | $3.0 \times 10^{-8}$ |
| H—Arg(Tos)—Pro—Hyp—Gly—Thia—Ser-(D)-Tic—Oic—Arg—OH | $1.8 \times 10^{-8}$ |
| H-(D)-Arg—Arg—Pro—Hyp—Gly—Phe—Ser-(D)-Phe—Oic—Arg—OH | $1.4 \times 10^{-8}$ |
| H-(D)-Arg—Arg—Pro—Hyp—Gly—Thia—Ser-(D)-Phe—Oic—Arg—OH | $1.4 \times 10^{-8}$ |

TABLE 1-continued

| Compound | IC$_{50}$ [M] |
| --- | --- |
| H-(D)-Arg—Arg—Pro—Pro—Gly—Phe—Ser-(D)-(p-Cl)Phe—Oic—Arg—OH | $8 \times 10^{-8}$ |
| H-(D)-Arg—Arg—Pro—Hyp—Gly—Leu—Ser-(D)-Tic—Oic—Arg—OH | $5.9 \times 10^{-9}$ |
| H-(D)-Arg—Arg—Pro—Hyp—Gly—Cha—Ser-(D)-Tic—Oic—Arg—OH | $3.7 \times 10^{-8}$ |
| H-(D)-Arg—Arg—Pro—Hyp—Gly—Tbg—Ser-(D)-Tic—Oic—Arg—OH | $6.0 \times 10^{-6}$ |

The therapeutic utility of the peptides according to the invention includes all pathological states which are mediated, caused or supported by bradykinin and bradykinin-related peptides. This includes, inter alia, traumas, such as wounds, burns, rashes, erythemas, edemas, angina, tonsillitis, arthritis, asthma, allergies, rhinitis, shock, inflammations, low blood pressure, pain, itching, pruritus, and changed sperm motility.

The invention therefore also relates to the use of peptides of the formula I as medicaments, and to pharmaceutical preparations which contain these compounds.

Pharmaceutical preparations contain an effective amount of the active substance of the formula I—individually or in combination—together with an inorganic or organic pharmaceutically utilizable excipient.

Administration can be carried out enterally, parenterally, such as, for example, subcutaneously, i.m. or i.v., sublingually, epicutaneously, nasally, rectally, intravaginally, intrabuccally or by inhalation. The dosage of the active substance depends on the mammal species, the body weight, age and on the manner of administration.

The pharmaceutical preparations of the present invention are prepared in solution, mixing, granulating or tablet coating processes known per se.

For oral administration or application to the mucosa, the active compounds are mixed with the customary additives for this, such as excipients, stabilizers or inert diluents, and brought into suitable forms for administration, such as tablets, coated tablets, hard gelatin capsules, aqueous, alcoholic or oily suspensions or aqueous, alcoholic or oily solutions, by customary methods. Inert excipients which may be used are, for example, gum arabic, magnesia, magnesium carbonate, potassium phosphate, lactose, glucose, magnesium stearyl fumarate or starch, in particular maize starch. In this case, the preparation may be present both as dry and moist granules. Suitable oily excipients or solvents are, for example, vegetable or animal oils, such as sunflower oil and cod liver oil.

A preparation for topical application may be present as an aqueous or oily solution, lotion, emulsion or gel, ointment or fatty ointment or, if possible, in spray form, it being possible to improve the adhesion, if desired, by addition of a polymer.

For the intranasal form of administration, the compounds are mixed with the customary auxiliaries for this, such as stabilizers or inert diluents, and brought into suitable forms for administration, such as aqueous, alcoholic or oily suspensions or aqueous, alcoholic or oily solutions, by customary methods. Chelating agents, ethylenediamine-N,N,N',N'-tetraacetic acid, citric acid, tartaric acid or their salts may be added to aqueous intranasal preparations. Administration of the nasal solutions can be carried out by means of metered atomizers or as nasal drops, having a viscosity increasing component, or nasal gels or nasal creams.

For administration by inhalation, atomizers or pressurized gas packs using inert carrier gases can be used.

For intravenous, subcutaneous, epicutaneous or intradermal administration, the active compounds or their physiologicaLLy tolerable salts, if desired with the pharmaceutically customary auxiliaries, for example for isotonisizing or adjusting pH, and solubilizers, emulsifiers or other auxiliaries, are brought into solution, suspension or emulsion.

Because of the short half-lives of some of the medicaments described in body fluids, the use of injectable sustained release preparations is efficient. Medicament forms which may be used are, for example, oily crystal suspensions, microcapsules, rods or implants, it being possible to synthesize the latter from tissue-compatible polymers, in particular biodegradable polymers, such as, for example, those based on polylactic acid/polyglycolic acid copolymers or human albumin.

A suitable dose range for forms for topical application and administration by inhalation are solutions containing 0.01–5 mg/ml, and with forms for systemic administration 0.01–10 mg/kg is suitable.

List of abbreviations:

The abbreviations used for amino acids correspond to the three-letter code customary in peptide chemistry as described in Europ. J. Biochem. 138, 9 (1984). Additionally used abbreviations are listed below.

| | |
| --- | --- |
| Acm | Acetamidomethyl |
| ε-Ahx | ε-Aminohexanoyl |
| Aoc | cis, endo-2-Azabicyclo[3.3.0]octane-3-S-carbonyl |
| Boc | tert-Butyloxycarbonyl |
| But | tert-Butyl |
| Bzl | Benzyl |
| CDF | Chloro-(D)-phenylalanyl |
| Cha | Cyclohexylalanyl |
| Chg | Cyclohexylglycyl |
| Cl-Z | 4-Chlorobenzyloxycarbonyl |
| DMF | Dimethylformamide |
| DOMT | O-Methyl-(D)-threonyl |
| Dnp | 2,4-Dinitrophenyl |
| Fmoc | 9-Fluorenylmethoxycarbonyl |
| MDY | O-Methyl-(D)-tyrosyl |
| Me | Methyl |
| 4-Mebzl | 4-Methylbenzyl |
| Mtr | 4-Methoxy-2,3,6-trimethylphenylsulfonyl |
| Mts | Mesitylene-2-sulfonyl |
| Nal | 1- or 2-napthylalanyl |
| NMP | N-Methylpyrrolidine |
| Npg | Neopentylglycyl |
| Oic | cis-endo-octahydroindol-2-ylcarbonyl |
| Opr | Isoxazolidin-3-ylcarbonyl |
| Pal | 2- or 3-pyridylalanyl |
| Pmc | 2,2,5,7,8-Pentamethylchroman-6-sulfonyl |
| Tbg | tert-Butylglycyl |
| Tes | 4-Methylphenylsulfonyl |
| Thia | 2-Thienylalanyl |
| Tic | 1,2,3,4-Tetrahydroisoquinolin-3-ylcarbonyl |
| Trt | Trityl |

The following examples are intended to illustrate the preferred methods for solid phase synthesis of the peptides according to the invention, without limiting the invention thereto.

In the following examples 1–195, the amino acid derivatives below were used:

Fmoc-Arg(Mtr)-OH, Boc-(D)-Arg-OH, Fmoc-Arg(Pmc)-OH, Fmoc-Hyp-OH, Fmoc-Pro-OObt, Fmoc-Gly-OObt, Fmoc-Phe-OObt, Fmoc-Ser(tBu)-OObt, Fmoc-(D)-Tic-OH, Fmoc-Gln-OH, Fmoc-Aoc-OH, Fmoc-Thia-OH, Fmoc-Opr-OH, Fmoc-(D)-Asn-OH, Fmoc-β-Ala-OH, Fmoc-Oic-OH.

EXAMPLE 1

H-(D)-Arg-Arg-Hyp-Pro-Gly-Phe-Ser-(D)-Tic-Phe-Arg-OH was synthesized stepwise using a peptide synthesizer model 430 A from Applied Biosystems by the Fmoc method on a p-benzyloxybenzyl alcohol resin from Novabiochem (loading about 0.5 mmol/g of resin) esterified with Fmoc-Arg(Mtr)-OH. 1 g of the resin was employed and the synthesis was carried out with the aid of a synthesis program modified for the Fmoc method.

In each case 1 mmol of the amino acid derivative having a free carboxyl group together with 0.95 mmol of HOObt was weighed into the cartridges of the synthesizer. The preactivation of these amino acids was carried out directly in the cartridges by dissolving in 4 ml of DMF and adding 2 ml of a 0.55 mol solution of diisopropylcarbodiimide in DMF.

The HOObt esters of the other amino acids were dissolved in 6 ml of NMP and then similarly coupled to the resin previously deblocked using 20% piperidine in DMF, like the amino acids preactivated in situ. After completion of the synthesis, the peptide was split off from the resin using thioanisole and ethanedithiol as cation entrainers, with simultaneous removal of the side chain protective groups using trifluoroacetic acid. The residue obtained after stripping off the trifluoroacetic acid was repeatedly digested with ethyl acetate and centrifuged. The residue which remained was chromatographed on ®Sephadex LH 20 using 10% strength acetic acid. The fractions containing the pure peptide were combined and freeze-dried.

MS(FAB): 1294 (M+H)

The peptides of Examples 2 to 24 below were prepared and purified analogously to Example 1.

EXAMPLE 2

H-(D)-Arg-Arg-Hyp-Pro-Gly-Phe-(D)-Ser-(D)-Tic-Phe-Arg-OH
MS(FAB): 1294 (M+H)

EXAMPLE 3

H-(D)-Arg-Arg-Hyp-Pro-Gly-Thia-Ser-(D)-Tic-Thia-Arg-OH
MS(FAB): 1306 (M+H)

EXAMPLE 4

H-(D)-Arg-Arg-Pro-Hyp-Gly-Phe-Ser-(D)-Tic-Phe-Arg-OH
MS(FAB): 1294 (M+H)

EXAMPLE 5

H-(D)-Arg-Arg-Hyp-Pro-Gly-Phe-Gln-(D)-Tic-Phe-Arg-OH
MS(FAB): 1335 (M+H)

EXAMPLE 6

H-(D)-Arg-Arg-Hyp-Pro-Gly-Phe-Ser-(D)-Tic-Pro-Arg-OH
MS(FAB): 1244 (M+H)

EXAMPLE 7

H-(D)-Arg-Arg-Hyp-Pro-Gly-Phe-Trp-(D)-Tic-Phe-Arg-OH
MS(FAB): 1393 (M+H)

EXAMPLE 8

H-(D)-Arg-Arg-Hyp-Pro-Gly-Thia-Ser-(D)-Tic-Pro-Arg-OH
MS(FAB): 1250 (M+H)

EXAMPLE 9

H-(D)-Arg-Arg-Hyp-Pro-Gly-Thia-(D)-Asn-(D)-Tic-Thia-Arg-OH
MS(FAB): 1333 (M+H)

EXAMPLE 10

H-(D)-Arg-Arg-Hyp-Pro-Gly-Thia-Opr-(D)-Tic-Thia-Arg-OH
MS(FAB): 1301 (M+H)

EXAMPLE 11

H-(D)-Arg-Arg-Hyp-Pro-Gly-Thia-(D)-Gln-(D)-Tic-Thia-Arg-OH
MS(FAB): 1347 (M+H)

EXAMPLE 12

H-(D)-Arg-Arg-Hyp-Pro-Gly-Thia-Ser-Gly-(D)-Tic-Pro-Arg-OH
MS(FAB): 1307 (M+H)

EXAMPLE 13

H-(D)-Arg-Arg-Hyp-Pro-Gly-Thia-Ser-(D)-Tic-Pro-Phe-OH
MS(FAB): 1241 (M+H)

EXAMPLE 14

H-(D)-Arg-Arg-Hyp-Pro-Gly-Thia-Ser-(D)-Tic-Pro-Phe-Arg-OH
MS(FAB): 1397 (M+H)

EXAMPLE 15

H-(D)-Arg-Arg-Hyp-Pro-Gly-Thia-Ser-β-Ala-(D)-Tic-Pro-Arg-OH
MS(FAB): 1321 (M+H)

EXAMPLE 16

H-(D)-Arg-Arg-Hyp-Pro-Gly-Thia-Gly-(D)-Tic-Pro-Arg-OH
MS(FAB): 1220 (M+H)

EXAMPLE 17

H-(D)-Arg-Arg-Aoc-Pro-Gly-Thia-Ser-(D)-Tic-Thia-Arg-OH
MS(FAB): 1330 (M+H)

EXAMPLE 18

H-(D)-Arg-Arg-Pro-Aoc-Gly-Thia-Ser-(D)-Tic-Thia-Arg-OH
MS(FAB): 1330 (M+H)

EXAMPLE 19

H-(D)-Arg-Arg-Hyp-Pro-Gly-Thia-Ser-(D)-Tic-Aoc-Arg-OH
MS(FAB): 1290 (M+H)

EXAMPLE 20

H-(D)-Arg-Arg-Opr-Pro-Gly-Thia-Ser-(D)-Tic-Pro-Arg-OH
MS(FAB): 1236 (M+H)

EXAMPLE 21

H-(D)-Arg-Arg-Pro-Opr-Gly-Thia-Ser-(D)-Tic-Pro-Arg-OH
MS(FAB): 1236 (M+H)

EXAMPLE 22

H-(D)-Arg-Arg-Hyp-Pro-Gly-Thia-Ser-(D)-Tic-Opr-Arg-OH
MS(FAB): 1252 (M+H)

EXAMPLE 23

H-(D)-Arg-(D)-Arg-Hyp-Pro-Gly-Thia-Ser-(D)-Tic-Aoc-Arg-OH
MS(FAB): 1290 (M+H)

EXAMPLE 24

H-(D)-Arg-Arg-Pro-Hyp-Gly-Thia-Ser-(D)-Tic-Aoc-Arg-OH
MS(FAB): 1290 (M+H)

EXAMPLES 25–27

H-(D)-Arg-Arg(Mtr)-Pro-Hyp-Gly-Phe-Ser-(D)-Tic-Phe-Arg-OH,
H-(D)-Arg-Arg(Mtr)-Pro-Hyp-Gly-Phe-Ser-(D)-Tic-Phe-Arg(Mtr)-OH and
H-(D)-Arg-Arg-Pro-Hyp-Gly-Phe-Ser-(D)-Tic-Phe-Arg(Mtr)-OH were prepared analogously to Example 1, the splitting off of the side chain protective groups and the peptide from the resin by means of trifluoroacetic acid being limited to 30 minutes at room temperature. Under the conditions thus selected, only a negligible splitting off of the Mtr protective group on the arginine took place. The partially deblocked peptides were separated by chromatography on reverse phase material and purified.

EXAMPLE 25

H-(D)-Arg-Arg(Mtr)-Pro-Hyp-Gly-Phe-Ser-(D)-Tic-Phe-Arg-OH
MS(FAB): 1506 (M+H)

EXAMPLE 26

H-(D)-Arg-Arg(Mtr)-Pro-Hyp-Gly-Phe-Ser-(D)-Tic-Phe-Arg(Mtr)-OH
MS(FAB): 1718 (M+H)

EXAMPLE 27

H-(D)-Arg-Arg-Pro-Hyp-Gly-Phe-Ser-(D)-Tic-Phe-Arg(Mtr)-OH
MS(FAB): 1506 (M+H)

The peptides of Examples 28–31 below were prepared and purified analogously to Examples 25–27.

EXAMPLE 28

H-(D)-Arg-Arg(Mtr)-Hyp-Pro-Gly-Thia-Ser-(D)-Tic-Pro-Arg-OH
MS(FAB): 1462 (M+H)

EXAMPLE 29

H-(D)-Arg-Arg-Hyp-Pro-Gly-Thia-Ser-(D)-Tic-Pro-Arg(Mtr)-OH
MS(FAB): 1462 (M+H)

EXAMPLE 30

H-(D)-Arg-Arg(Mtr)-Hyp-Pro-Gly-Thia-Ser-(D)-Tic-Pro-Phe-OH
MS(FAB): 1453 (M+H)

EXAMPLE 31

H-(D)-Arg-Arg(Mtr)-Hyp-Pro-Gly-Thia-Ser-(D)-Tic-Aoc-Arg-OH
MS(FAB): 1502 (M+H)

EXAMPLE 32

H-Arg-Hyp-Pro-Gly-Phe-Ser-(D)-Tic-Phe-NH—(CH$_2$)$_4$—NH$_2$.

The peptide synthesis was carried out on 1 g of an aminomethyl resin which was modified with an attachment group of the type

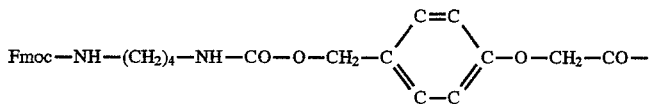

described in EP-A 264,802, using Fmoc-amino acid-OObt esters with an automatic peptide synthesizer (model 430A from Applied Biosystems) and synthesis programs which have themselves been modified. To this end, in each case 1 mmol of the appropriate amino acid derivative was weighed into the cartridges provided by the manufacturer, and Fmoc-Arg(Mtr)-OH, Fmoc-Hyp-OH and Fmoc-(D)-Tic-OH were weighed into the cartridges together with 0.95 mmol of HOObt. The preactivation of these amino acids in situ was carried out directly in the cartridges by dissolving in 4 ml of DMF and adding 2 ml of a 0.55M solution of diisopropyl-carbodiimide in DMF. The HOObt esters of the other amino acids were dissolved in 6 ml of NMP and then coupled to the resin previously deblocked using 20% piperidine in DMF, like the amino acids preactivated in situ, the amino acids activated in situ being doubly coupled. After completion of synthesis, the peptide 4-aminobutylamide was split off from the resin with simultaneous removal of the side chain protective groups with trifluoroacetic acid which contained thioanisole and m-cresol as cation entrainers. The residue obtained after stripping off the trifluoroacetic acid was repeatedly digested with ethyl acetate and centrifuged. The crude peptide which remained was chromatographed on ®Sephadex G25 using 1N acetic acid. The fractions containing the pure peptide were combined and freeze-dried.

The compounds of Examples 33–35 were prepared analogously to Example 32.

EXAMPLE 33

H-D-Arg-Arg-Hyp-Pro-Gly-Phe-Ser-(D)-Tic-Phe-NH—(CH$_2$)4—NH$_2$
MS(FAB): 1208 (M+H)

EXAMPLE 34

HOOC-(CH$_2$)$_2$—CO-Arg-Hyp-Pro-Gly-Phe-Ser-(D)-Tic-Phe-NH—(CH$_2$)$_4$—NH$_2$
MS(FAB): 1152 (M+H)

EXAMPLE 35

HOOC-(CH$_2$)$_2$—CO-(D)-Arg-Arg-HYP-Pro-Gly-Phe-Ser-(D)-Tic-Phe-NH—(CH$_2$)$_4$—NH$_2$
MS(FAB): 1308(M+H)

The examples 36 to 161 were synthesized according to the method described under Example 1.

EXAMPLE 36

H-(D)-Arg-Arg-Hyp-Pro-Gly-Thia-Ser-Gly-(D)-Tic-Pro-Arg-OH
MS(FAB): 1307 (M+H)

EXAMPLE 37

H-(D)-Arg-Arg-Pro-Hyp-Gly-Thia-Ser-Gly-(D)-Tic-pro-Arg-OH
MS FAB): 1307 (M+H)

EXAMPLE 38

H-(D)-Arg-Arg-Hyp-Pro-Gly-Thia-Ser-(D)-Tic-Pro-Phe-OH
MS(FAB): 1241 (M+H)

EXAMPLE 39

H-(D)-Arg-Arg-Hyp-Pro-Gly-Thia-Ser-β-Ala-(D)-Tic-Aoc-Arg-OH
MS(FAB): 1361 (M+H)

EXAMPLE 40

H-(D)-Arg-Arg-Pro-Hyp-Gly-Thia-Ser-β-Ala-(D)-Tic-Aoc-Arg-OH
MS(FAB): 1361 (M+H)

EXAMPLE 41

H-(D)-Arg-Arg-Hyp-Pro-Gly-Thia-Ser-(D)-Tic-Pro-Phe-Arg-OH
MS(FAB): 1397 (M+H)

EXAMPLE 42

H-(D)-Arg-Arg-Pro-Hyp-Gly-Thia-Ser-(D)-Tic-Pro-Phe-Arg-OH
MS(FAB): 1397 (M+H)

EXAMPLE 43

H-(D)-Arg-Arg-Pro-Hyp-Gly-Thia-Gly-(D)-Tic-Aoc-Arg-OH
MS(FAB): 1260 (M+H)

EXAMPLE 44

H-(D)-Arg-Arg-Hyp-Pro-Gly-Thia-Gly-(D)-Tic-Aoc-Arg-OH
MS(FAB): 1260 (M+H)

EXAMPLE 45

H-(D)-Arg-(D)-Arg-Hyp-Pro-Gly-Thia-Ser-(D)-Tic-Aoc-Arg-OH
MS(FAB): 1290 (M+H)

EXAMPLE 46

H-(D)-Arg-(D)-Arg-Pro-Hyp-Gly-Thia-Ser-(D)-Tic-Aoc-Arg-OH
MS(FAB): 1290 (M+H)

EXAMPLE 47

H-(D)-Arg-Arg-Hyp-Pro-Gly-Thia-Ser-(D)-Tic-Tic-Arg-OH
MS(FAB): 1312 (M+H)

EXAMPLE 48

H-(D)-Arg-Arg-Pro-Hyp-Gly-Thia-Ser-(D)-Tic-Tic-Arg-OH
MS(FAB): 1312 (M+H)

EXAMPLE 49

H-(D)-Arg-Arg-Pro-Pro-Gly-Thia-Ser-(D)-Tic-Aoc-Arg-OH
MS(FAB): 1274 (M+H)

EXAMPLE 50

H-(D)-Arg-Arg-Hyp-Pro-Gly-Thia-(D)-Tic-Aoc-Arg-OH
MS(FAB): 1203 (M+H)

EXAMPLE 51

H-(D)-Arg-Arg-Hyp-Pro-Gly-Aoc-Ser-(D)-Tic-Aoc-Arg-OH
MS(FAB): 1274 (M+H)

EXAMPLE 52

H-(D)-Arg-Arg-Hyp-Pro-Gly-Thia-β-Ala-(D)-Tic-Aoc-Arg-OH
MS(FAB): 1274 (M+H)

EXAMPLE 53

H-(D)-Arg-Arg-Pro-Hyp-Gly-Thia-β-Ala-(D)-Tic-Aoc-Arg-OH
MS(FAB): 1274 (M+H)

EXAMPLE 54

H-(D)-Arg-Arg-Hyp-Pro-Gly-Asp-Ser-(D)-Tic-Aoc-Arg-OH
MS(FAB): 1252 (M+H)

EXAMPLE 55

H-(D)-Arg-Arg-Pro-Hyp-Gly-Asp-Ser-(D)-Tic-Aoc-Arg-OH
MS(FAB): 1252 (M+H)

EXAMPLE 56

H-(D)-Arg-Arg-Hyp-Pro-Gly-Trp-Ser-(D)-Tic-Aoc-Arg-OH
MS(FAB): 1323.7 (M+H)

EXAMPLE 57

H-(D)-Tyr-Arg-Pro-Hyp-Gly-Thia-Ser-(D)-Tic-Aoc-Arg-OH
MS(FAB): 1297.7 (M+H)

EXAMPLE 58

H-(D)-Arg-Arg-Pro-Hyp-Gly-Thia-Ser-(D)-Tic-(D)-Oic-Arg-OH
MS(FAB): 1304.6 (M+H)

EXAMPLE 59

H-(D)-Arg-Arg-Pro-Hyp-Gly-Thia-Ser-(D)-Tic-Oic-Arg-OH
MS(FAB): 1304.6 (M+H)

EXAMPLE 60

H-(D)-Arg-Arg-Pro-Pro-Gly-Thia-Ser-(D)-Tic-Oic-Arg-OH
MS(FAB): 1289 (M+H)

EXAMPLE 61

H-(D)-Arg-Lys-Pro-Hyp-Gly-Thia-Ser-(D)-Tic-Aoc-Arg-OH
MS(FAB): 1262 (M+H)

EXAMPLE 62

H-(D)-Arg-Lys-Pro-Hyp-Gly-Thia-Ser-(D)-Tic-Oic-Arg-OH
MS(FAB): 1276 (M+H)

EXAMPLE 63

H-(D)-Arg-Lys-Pro-Pro-Gly-Thia-Ser-(D)-Tic-Oic-Arg-OH
MS(FAB): 1260 (M+H)

EXAMPLE 64

H-(D)-Arg-Arg-Pro-Hyp-Gly-Phe-Ser-(D)-Tic-Oic-Arg-OH
MS(FAB): 1298 (M+H)

EXAMPLE 65

H-(D)-Arg-Arg-Hyp-Pro-Gly-Phe-Ser-(D)-Tic-Oic-Arg-OH
MS(FAB): 1298 (M+H)

EXAMPLE 66

H-(D)-Arg-Arg-Pro-Pro-Gly-Phe-Ser-(D)-Tic-Oic-Arg-OH
MS(FAB): 1282 (M+H)

EXAMPLE 67

H-(D)-Arg-Arg(NO$_2$)-Pro-Hyp-Gly-Phe-Ser-(D)-Tic-Aoc-Arg-OH
MS(FAB): 1329.7 (M+H)

EXAMPLE 68

H-(D)-Arg-Arg(NO$_2$)-Pro-Hyp-Gly-Phe-Ser-(D)-Tic-Oic-Arg-OH
MS(FAB): 1343 (M+H)

EXAMPLE 69

H-(D)-Arg-Arg(NO$_2$)-Pro-Pro-Gly-Phe-Ser-(D)-Tic-Oic-Arg-OH
MS(FAB): 1327 (M+H)

EXAMPLE 70

H-(D)-Arg-Arg-(NO$_2$)-Pro-Pro-Gly-Thia-Ser-(D)-Tic-Oic-Arg-OH
MS(FAB): 1333 (M+H)

EXAMPLE 71

H-(D)-Arg-Arg(NO$_2$)-Pro-Hyp-Gly-Thia-Ser-(D)-Tic-Oic-Arg-OH
MS(FAB): 1349 (M+H)

EXAMPLE 72

H-Arg(Tos)-Pro-Hyp-Gly-Thia-Ser-D-Tic-Oic-Arg-OH
MS(FAB): 1302 (M+H)

EXAMPLE 73

H-Arg-Pro-Hyp-Gly-Phe-Ser-D-Tic-Oic-Arg-OH
MS(FAB): 1142 (M+H)

EXAMPLE 74

H-Lys(—CO—NH—C$_6$H$_5$)-Pro-Hyp-Gly-Phe-Ser-D-Tic-Oic-Arg-OH
MS(FAB): 1233 (M+H)

EXAMPLE 75

H-Arg(Tos)-Pro-Hyp-Gly-Phe-Ser-D-Tic-Oic-Arg-OH
MS(FAB): 1296 (M+H)

EXAMPLE 76

H-Lys(Nicotinoyl)-Pro-Hyp-Gly-Phe-Ser-D-Tic-Oic-Arg-OH
MS(FAB): 1219 (M+H)

EXAMPLE 77

H-Arg(Tos)-Pro-Hyp-Gly-Phe-Ser-D-Tic-Aoc-Arg-OH
MS(FAB): 1282 (M+H)

EXAMPLE 78

Ac-Arg(Tos)-Pro-Hyp-Gly-Phe-Ser-D-Tic-Aoc-Arg-OH
MS(FAB): 1324 (M+H)

EXAMPLE 79

H-D-Arg-Arg(Tos)-Pro-Hyp-Gly-Phe-Ser-D-Tic-Aoc-Arg-OH
MS(FAB): 1438 (M+H)

EXAMPLE 80

H-Arg(Tos)-Hyp-Pro-Gly-Thia-Ser-D-Tic-Oic-Arg-OH
MS(FAB): 1302 (M+H)

EXAMPLE 81

H-Arg-Hyp-Pro-Gly-Phe-Ser-D-Tic-Oic-Arg-OH
MS(FAB): 1142 (M+H)

EXAMPLE 82

H-Lys(—CO—NH—C$_6$H$_5$)-Hyp-Pro-Gly-Phe-Ser-D-Tic-Oic-Arg-OH
MS(FAB): 1233 (M+H)

EXAMPLE 83

H-Arg(Tos)-Hyp-Pro-Gly-Phe-Ser-D-Tic-Oic-Arg-OH
MS(FAB): 1296 (M+H)

EXAMPLE 84

H-Lys(Nicotinoyl)-Hyp-Pro-Gly-Phe-Ser-D-Tic-Oic-Arg-OH
MS(FAB): 1219 (M+H)

EXAMPLE 85

H-Arg(Tos)-Hyp-Pro-Gly-Phe-Ser-D-Tic-Aoc-Arg-OH
MS(FAB): 1282 (M+H)

EXAMPLE 86

Ac-Arg(Tos)-Hyp-Pro-Gly-Phe-Ser-D-Tic-Aoc-Arg-OH
MS(FAB): 1324 (M+H)

EXAMPLE 87

H-D-Arg-Arg(Tos)-Hyp-Pro-Gly-Phe-Ser-D-Tic-Aoc-Arg-OH
MS(FAB): 1438 (M+H)

EXAMPLE 88

H-Arg(Tos)-Pro-Pro-Gly-Thia-Ser-D-Tic-Oic-Arg-OH
MS(FAB): 1286 (M+H)

EXAMPLE 89

H-Arg-Pro-Pro-Gly-Phe-Ser-D-Tic-Oic-Arg-OH
MS(FAB): 1126 (M+H)

EXAMPLE 90

H-Lys(—CO—NH—C$_6$H$_5$)-Pro-Pro-Gly-Phe-Ser-D-Tic-Oic-Arg-OH
MS(FAB): 1217 (M+H)

EXAMPLE 91

H-Arg(Tos)-Pro-Pro-Gly-Phe-Ser-D-Tic-Oic-Arg-OH
MS(FAB): 1280 (M+H)

EXAMPLE 92

H-Lys(Nicotinoyl)-Pro-Pro-Gly-Phe-Ser-D-Tic-Oic-Arg-OH
MS(FAB): 1203 (M+H)

EXAMPLE 93

H-Arg(Tos)-Pro-Pro-Gly-Phe-Ser-D-Tic-Aoc-Arg-OH
MS(FAB): 1266 (M+H)

EXAMPLE 94

Ac-Arg(Tos)-Pro-Pro-Gly-Phe-Ser-D-Tic-Aoc-Arg-OH
MS(FAB): 1308 (M+H)

EXAMPLE 95

H-D-Arg-Arg(Tos)-Pro-Pro-Gly-Phe-Ser-D-Tic-Aoc-Arg-OH
MS(FAB): 1422 (M+H)

EXAMPLE 96

H-Arg-Pro-Hyp-Gly-Thia-Ser-D-Tic-Oic-Arg-OH
MS(FAB): 1148 (M+H)

EXAMPLE 97

H-Lys(—CO—NH—C$_6$H$_5$)-Pro-Hyp-Gly-Thia-Ser-D-Tic-Oic-Arg-OH
MS(FAB): 1239 (M+H)

EXAMPLE 98

H-Lys(Nicotinoyl)-Pro-Hyp-Gly-Thia-Ser-D-Tic-Oic-Arg-OH
MS(FAB): 1225 (M+H)

EXAMPLE 99

H-Arg(Tos)-Pro-Hyp-Gly-Thia-Ser-D-Tic-Aoc-Arg-OH
MS(FAB): 1288 (M+H)

EXAMPLE 100

Ac-Arg(Tos)-Pro-Hyp-Gly-Thia-Ser-D-Tic-Aoc-Arg-OH
MS(FAB): 1330 (M+H)

EXAMPLE 101

H-D-Arg-Arg(Tos)-Pro-Hyp-Gly-Thia-Ser-D-Tic-Aoc-Arg-OH
MS(FAB): 1444 (M+H)

EXAMPLE 102

H-Arg-Hyp-Pro-Gly-Thia-Ser-D-Tic-Oic-Arg-OH
MS(FAB): 1148 (M+H)

EXAMPLE 103

H-Lys(—CO—NH—C$_6$H$_5$)-Hyp-Pro-Gly-Thia-Ser-D-Tic-Oic-Arg-OH
MS(FAB): 1239 (M+H)

EXAMPLE 104

H-Lys(Nicotinoyl)-Hyp-Pro-Gly-Thia-Ser-D-Tic-Oic-Arg-OH
MS(FAB): 1225 (M+H)

EXAMPLE 105

H-Arg(Tos)-Hyp-Pro-Gly-Thia-Ser-D-Tic-Aoc-Arg-OH
MS(FAB): 1288 (M+H)

EXAMPLE 106

Ac-Arg(Tos)-Hyp-Pro-Gly-Thia-Ser-D-Tic-Aoc-Arg-OH
MS(FAB): 1330 (M+H)

EXAMPLE 107

H-D-Arg-Arg(Tos)-Hyp-Pro-Gly-Thia-Ser-D-Tic-Aoc-Arg-OH
MS(FAB): 1440 (M+H)

EXAMPLE 108

H-Lys(—CO—NH—C$_6$H$_5$)-Pro-Pro-Gly-Thia-Ser-D-Tic-Oic-Arg-OH
MS(FAB): 1225 (M+H)

EXAMPLE 109

H-Lys(Nicotinoyl)-Pro-Pro-Gly-Thia-Ser-D-Tic-Oic-Arg-OH
MS(FAB): 1209 (M+H)

EXAMPLE 110

H-Arg(Tos)-Pro-Pro-Gly-Thia-Ser-D-Tic-Aoc-Arg-OH
MS(FAB): 1272 (M+H)

EXAMPLE 111

Ac-Arg(Tos)-Pro-Pro-Gly-Thia-Ser-D-Tic-Aoc-Arg-OH
MS(FAB): 1314 (M+H)

EXAMPLE 112

H-D-Arg-Arg(Tos)-Pro-Pro-Gly-Thia-Ser-D-Tic-Aoc-Arg-OH
MS(FAB): 1428 (M+H)

EXAMPLE 113

H-D-Arg-Lys(Nicotinoyl)-Pro-Pro-Gly-Thia-Ser-D-Tic-Oic-Arg-OH
MS(FAB): 1365 (M+H)

EXAMPLE 114

H-D-Arg-Lys(—CO—NH—$C_6H_5$)-Pro-Pro-Gly-Thia-Ser-D-Tic-Oic-Arg-OH
MS(FAB): 1379 (M+H)

EXAMPLE 115

H-D-Arg-Arg(Tos)-Pro-Pro-Gly-Thia-Ser-D-Tic-Oic-Arg-OH
MS(FAB): 1442 (M+H)

EXAMPLE 116

H-Lys-Lys-(Nicotinoyl)-Pro-Pro-Gly-Thia-Ser-D-Tic-Oic-Arg-OH
MS(FAB): 1337 (M+H)

EXAMPLE 117

H-Lys-Lys(-CO—NH—$C_6H_5$)-Pro-Pro-Gly-Thia-Ser-D-Tic-Oic-Arg-OH
MS(FAB): 1351 (M+H)

EXAMPLE 118

H-Lys-Arg(Tos)-Pro-Pro-Gly-Thia-Ser-D-Tic-Oic-Arg-OH
MS(FAB): 1414 (M+H)

EXAMPLE 119

H-D-Arg-Lys(Nicotinoyl)-Pro-Hyp-Gly-Thia-Ser-D-Tic-Oic-Arg-OH
MS(FAB): 1381 (M+H)

EXAMPLE 120

H-D-Arg-Lys(—CO—NH—$C_6H_5$)-Pro-Hyp-Gly-Thia-Ser-D-Tic-Oic-Arg-OH
MS(FAB) :2 1395 (M+H)

EXAMPLE 121

H-D-Arg-Arg(Tos)-Pro-Hyp-Gly-Thia-Ser-D-Tic-Oic-Arg-OH
MS(FAB): 1458 (M+H)

EXAMPLE 122

H-Lys-Lys(—CO—NH—$C_6H_5$)-Pro-Hyp-Gly-Thia-Ser-D-Tic-Oic-Arg-OH
MS(FAB): 1367 (M+H)

EXAMPLE 123

H-Lys-Lys(Nicotinoyl)-Pro-Hyp-Gly-Thia-Ser-D-Tic-Oic-Arg-OH
MS(FAB): 1353 (M+H)

EXAMPLE 124

H-Lys-Arg(Tos)-Pro-Hyp-Gly-Thia-Ser-D-Tic-Oic-Arg-OH
MS(FAB): 1430 (M+H)

EXAMPLE 125

H-D-Arg-Lys(Nicotinoyl)-Pro-Pro-Gly-Phe-Ser-D-Tic-Oic-Arg-OH
MS(FAB): 1359 (M+H)

EXAMPLE 126

H-D-Arg-Lys(—CO—NH—$C_6H_5$)-Pro-Pro-Gly-Phe-Ser-D-Tic-Oic-Arg-OH
MS(FAB): 1373 (M+H)

EXAMPLE 127

H-D-Arg-Arg(Tos)-Pro-Pro-Gly-Phe-Ser-D-Tic-Oic-Arg-OH
MS(FAB): 1436 (M+H)

EXAMPLE 128

H-Lys-Lys(Nicotinoyl)-Pro-Pro-Gly-Phe-Ser-D-Tic-Oic-Arg-OH
MS(FAB): 1331 (M+H)

EXAMPLE 129

H-Lys-Lys(—CO—NH—$C_6H_5$)-Pro-Pro-Gly-Phe-Ser-D-Tic-Oic-Arg-OH
MS(FAB): 1345 (M+H)

EXAMPLE 130

H-Lys-Arg(Tos)-Pro-Pro-Gly-Phe-Ser-D-Tic-Oic-Arg-OH
MS(FAB): 1408 (M+H)

EXAMPLE 131

H-D-Arg-Lys(Nicotinoyl)-Pro-Hyp-Gly-phe-Ser-D-Tic-Oic-Arg-OH
MS(FAB): 1375 (M+H)

EXAMPLE 132

H-D-Arg-Lys(—CO—NH—$C_6H_5$)-Pro-Hyp-Gly-Phe-Ser-D-Tic-Oic-Arg-OH
MS(FAB): 1389 (M+H)

EXAMPLE 133

H-D-Arg-Arg(Tos)-Pro-Hyp-Gly-Phe-Ser-D-Tic-Oic-Arg-OH
MS(FAB): 1452 (M+H)

EXAMPLE 134

H-Lys-Lys(Nicotinoyl)-Pro-Hyp-Gly-Phe-Ser-D-Tic-Oic-Arg-OH
MS(FAB): 1347 (M+H)

EXAMPLE 135

H-Lys-Lys(—CO—NH—$C_6H_5$)-Pro-Hyp-Gly-Phe-Ser-D-Tic-Oic-Arg-OH
MS(FAB): 1361 (M+H)

EXAMPLE 136

H-Lys-Arg(Tos)-Pro-Hyp-Gly-Phe-Ser-D-Tic-Oic-Arg-OH
MS(FAB): 1424 (M+H)

EXAMPLE 137

H-D-Arg-Orn(Nicotinoyl)-Pro-Pro-Gly-Thia-Ser-D-Tic-Oic-Arg-OH
MS(FAB): 1351 (M+H)

EXAMPLE 138

H-D-Arg-Orn(—CO—NH—$C_6H_5$)-Pro-Pro-Gly-Thia-Ser-D-Tic-Oic-Arg-OH
MS(FAB): 1428 (M+H)

EXAMPLE 139

H-Lys-Orn(Nicotinoyl)-Pro-Pro-Gly-Thia-Ser-D-Tic-Oic-Arg-OH
MS(FAB): 1323 (M+H)

EXAMPLE 140

H-Lys-Orn(—CO—NH—$C_6H_5$)-Pro-Pro-Gly-Thia-Ser-D-Tic-Oic-Arg-OH
MS(FAB): 1337 (M+H)

EXAMPLE 141

H-D-Arg-Orn(Nicotinoyl)-Pro-Hyp-Gly-Thia-Ser-D-Tic-Oic-Arg-OH
MS(FAB): 1367 (M+H)

EXAMPLE 142

H-D-Arg-Orn(—CO—NH—$C_6H_5$)-Pro-Hyp-Gly-Thia-Ser-D-Tic-Oic-Arg-OH
MS(FAB): 1381 (M+H)

EXAMPLE 143

H-Lys-Orn(Nicotinoyl)-Pro-Hyp-Gly-Thia-Ser-D-Tic-Oic-Arg-OH
MS(FAB): 1339 (M+H)

EXAMPLE 144

H-Lys-Orn(—CO—NH—$C_6H_5$)-Pro-Hyp-Gly-Thia-Ser-D-Tic-Oic-Arg-OH
MS(FAB): 1353 (M+H)

EXAMPLE 145

H-D-Arg-Orn(Nicotinoyl)-Pro-Pro-Gly-Phe-Ser-D-Tic-Oic-Arg-OH
MS(FAB): 1345 (M+H)

EXAMPLE 146

H-D-Arg-Orn(—CO—NH—$C_6H_5$)-Pro-Pro-Gly-Phe-Ser-D-Tic-Oic-Arg-OH
MS(FAB): 1359 (M+H)

EXAMPLE 147

H-Lys-Orn(Nicotinoyl)-Pro-Pro-Gly-Phe-Ser-D-Tic-Oic-Arg-OH
MS(FAB): 1317 (M+H)

EXAMPLE 148

H-Lys-Orn(—CO—NH—$C_6H_5$)-Pro-Pro-Gly-Phe-Ser-D-Tic-Oic-Arg-OH
MS(FAB): 1331 (M+H)

EXAMPLE 149

H-D-Arg-Orn(Nicotinoyl)-Pro-Hyp-Gly-Phe-Ser-D-Tic-Oic-Arg-OH
MS(FAB): 1361 (M+H)

EXAMPLE 150

H-D-Arg-Orn(—CO—NH—$C_6H_5$)-Pro-Hyp-Gly-Phe-Ser-D-Tic-Oic-Arg-OH
MS(FAB): 1375 (M+H)

EXAMPLE 151

H-Lys-Orn(Nicotinoyl)-Pro-Hyp-Gly-Phe-Ser-D-Tic-Oic-Arg-OH
MS(FAB): 1333 (M+H)

EXAMPLE 152

H-Lys-Orn(—CO—NH—$C_6H_5$)-Pro-Hyp-Gly-Phe-Ser-D-Tic-Oic-Arg-OH
MS(FAB): 1347 (M+H)

EXAMPLE 153

H-Lys-Lys-Pro-Pro-Gly-Thia-Ser-(D)-Tic-Aoc-Arg-OH
MS(FAB): 1218 (M+H)

EXAMPLE 154

H-Lys-Lys-Pro-Hyp-Gly-Thia-Ser-(D)-Tic-Aoc-Arg-OH
MS(FAB): 1234 (M+H)

EXAMPLE 155

H-Lys-Lys-Hyp-Pro-Gly-Thia-Ser-(D)-Tic-Aoc-Arg-OH
MS(FAB): 1234 (M+H)

EXAMPLE 156

H-Lys-Lys-Pro-Pro-Gly-Phe-Ser-(D)-Tic-Aoc-Arg-OH
MS(FAB): 1212 (M+H)

EXAMPLE 157

H-Lys-Lys-Pro-Hyp-Gly-Phe-Ser-(D)-Tic-Aoc-Arg-OH
MS(FAB): 1228 (M+H)

EXAMPLE 158

H-Lys-Lys-Pro-Pro-Gly-Thia-Ser-(D)-Tic-Oic-Arg-OH
MS(FAB): 1232 (M+H)

EXAMPLE 159

H-Lys-Lys-Pro-Hyp-Gly-Thia-Ser-(D)-Tic-Oic-Arg-OH
MS(FAB) :=1248 (M+H)

EXAMPLE 160

H-Lys-Lys-Hyp-Pro-Gly-Thia-Ser-(D)-Tic-Oic-Arg-OH
MS(FAB): 1226 (M+H)

EXAMPLE 161

H-Lys-Lys-Pro-Hyp-Gly-Phe-Ser-(D)-Tic-Oic-Arg-OH
MS(FAB): 1242 (M+H)

The Examples 162–164 were prepared analogously to Example 32 using the resin having the structure

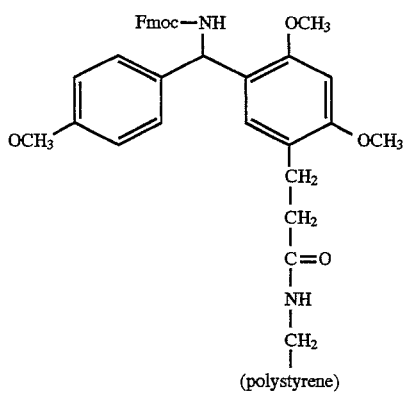

described in EP-A 322,348.

EXAMPLE 162

H-D-Arg-Arg-Pro-Hyp-Gly-Phe-Ser-D-Tic-Aoc-Arg-NH$_2$
MS(FAB): 1283 (M+H)

EXAMPLE 163

H-D-Arg-Arg-Hyp-Pro-Gly-Phe-Ser-D-Tic-Aoc-Arg-NH$_2$
MS(FAB): 1283 (M+H)

EXAMPLE 164

H-D-Arg-Arg-Pro-Pro-Gly-Phe-Ser-D-Tic-Aoc-Arg-NH$_2$
MS(FAB): 1267 (M+H)

The compounds of Examples 165–194 were prepared analogously to Example 1.

EXAMPLE 165

H-D-Arg-Arg-Pro-Pro-Gly-Phe-Ser-D-Tic-Aoc-Arg-OH
MS(FAB): 1267 (M+H)

EXAMPLE 166

H-D-Arg-Arg-Pro-Hyp-Gly-Phe-Ser-D-Tic-Aoc-Arg-OH
MS(FAB): 1284 (M+H)

EXAMPLE 167

H-D-Arg-Lys(Z)-Pro-Hyp-Gly-Phe-Ser-D-Tic-Aoc-Arg-OH
MS(FAB): 1390.7 (M+H)

EXAMPLE 168

H-D-Arg-Lys-Pro-Hyp-Gly-Phe-Ser-D-Tic-Aoc-Arg-OH
MS(FAB): 1256.7 (M+H)

EXAMPLE 169

H-D-Arg-Ser(Rha)-Pro-Hyp-Gly-Phe-Ser-D-Tic-Aoc-Arg-OH
MS(FAB): 1361 (M+H)

EXAMPLE 170

H-D-Arg-Arg-Pro-Pro-Gly-Phe-Ser-D-Tic-Aoc-D-Ser(Rha)-OH
MS(FAB): 1345 (M+H)

EXAMPLE 171

H-D-Arg-Arg(Tos)-Pro-Hyp-Gly-Phe-Ser-D-Tic-Aoc-Arg(Mtr)-OH
MS(FAB): 1650.7 (M+H)

EXAMPLE 172

H-D-Arg-Arg-Hyp-Pro-Gly-Thia-Ser-D-Tic-D-Aoc-Arg-OH
MS(FAB): 1290 (M+H)

EXAMPLE 173

H-D-Arg-Arg-Pro-Hyp-Gly-Thia-Ser-D-Tic-D-Oic-Arg-OH
MS(FAB): 1304.7 (M+H)

EXAMPLE 174

H-D-Arg-Arg-ΔPro-Hyp-Gly-Thia-Ser-D-Tic-Oic-Arg-OH
MS(FAB): 1302.7 (M+H)

EXAMPLE 175

H-Arg-Arg-Pro-Hyp-Gly-Thia-Ser-D-Tic-Oic-Arg-OH
MS(FAB): 1304.7 (M+H)

EXAMPLE 176

4-hydroxyphenylpropionyl-D-Arg-Arg-Pro-Hyp-Gly-Thia-Ser-D-Tic-Oic-Arg-OH
MS(FAB): 1452.7 (M+H)

EXAMPLE 177

H-D-Arg-D-Arg-Pro-Hyp-Gly-Thia-Ser-D-Tic-Oic-Arg-OH
MS(FAB): 1304.7 (M+H)

EXAMPLE 178

H-D-Arg-Arg-D-Pro-Hyp-Gly-Thia-Ser-D-Tic-Oic-Arg-OH
MS(FAB): 1304.6 (M+H)

EXAMPLE 179

H-D-Arg-Arg-Pro-Hyp-Gly-Thia-Ser-D-Tic-Oic-D-Arg-OH
MS(FAB): 1304.9 (M+H)

EXAMPLE 180

H-D-Arg-Arg-Pro-Hyp-Gly-D-Thia-Ser-D-Tic-Oic-Arg-OH
MS(FAB): 1304.8 (M+H)

EXAMPLE 181

H-D-Arg-Pro-Hyp-Gly-Thia-Ser-D-Tic-Oic-Arg-OH
MS(FAB): 1148 (M+H)

EXAMPLE 182

H-D-Arg-Arg-Pro-Hyp-Gly-Thia-Ser-D-Tic-Oic-OH
MS(FAB): 1147 (M+H)

EXAMPLE 183

H-D-Arg-Arg-Pro-Hyp-Gly-Thia-D-Ser-D-Tic-Oic-Arg-OH
MS(FAB): 1304.7 (M+H)

EXAMPLE 184

Ac-D-Arg-Arg-Pro-Hyp-Gly-Thia-Ser-D-Tic-Oic-Arg-OH
MS(FAB): 1346.9 (M+H)

EXAMPLE 185

H-D-Arg-Arg(Mtr)-Hyp-Pro-Gly-Thia-Ser-D-Tic-Pro-Phe-OH
MS(FAB): 1454.9 (M+H)

EXAMPLE 186

H-D-Arg-Arg-Hyp-Pro-Gly-Thia-Gly-D-Tic-D,L-Oic-Arg-OH
MS(FAB): 1274 (M+H)

EXAMPLE 1872

H-D-Arg-Arg-Hyp-Pro-Gly-Thia-β-Ala-D-Tic-Aoc-Arg-OH
MS(FAB): 1354.6 (M+H)

EXAMPLE 188

H-D-Arg-Pro-Hyp-Gly-Phe-Ser-D-Tic-Oic-Arg-OH
MS(FAB): 1142.5 (M+H)

EXAMPLE 189

(4-benzoyl)phenoxyacetyl-D-Arg-Arg-Pro-Hyp-Gly-Thia-Ser-D-Tic-Oic-Arg-OH
MS(FAB): 1542.6 (M+H)

EXAMPLE 190

H-((4-benzoyl)benzoyl)-Lys-D-Arg-Arg-Pro-Hyp-Gly-Thia-Ser-D-Tic-Oic-Arg-OH
MS(FAB): 1640.9 (M+H)

EXAMPLE 191

H-D-Arg-Arg-Pro-Hyp-Gly-Thia-Cys-D-Tic-Oic-Arg-OH
MS(FAB): 1320.7 (M+H)

EXAMPLE 192

H-D-Arg-Arg-Pro-Hyp-Gly-Thia-Ser-D-Tic-(3aR,7aS)Oic-Arg-OH
MS(FAB): 1304.7 (M+H)

EXAMPLE 193

H-D-Arg-Arg-Pro-Hyp-Gly-Thia-Ser-D-Tic-(3aS,7aR)Oic-Arg-OH
MS(FAB): 1304.7 (M+H)

EXAMPLE 194

H-D-Arg-Arg-Pro-Hyp-Gly-Thia-Ser-D-Tic-Oic-NH$_2$
MS(FAB): 1147.6 (M+H)

EXAMPLE 195

H-Arg-Pro-Hyp-Gly-Thia-Ser-D-Tic-Oic-OH

The peptide of Example 195 was prepared analogously to Example 1, however, the peptide was split off from the resin as follows:

The peptide resin was treated with a mixture of m-cresole and dichloromethane (1:2) (about 2 ml/g resin) for 10 minutes to swell the resin. The trifluoroacetic acid (about i0 ml/g resin) and bromotrimethylsilane (about 0.8 ml/g) resin were added with stirring. After 1.5 h reaction time the mixture was filtered through a sintered glass funnel into ice cold methyl-tertbutylether. The precipitated crude peptide was collected by filtration, washed with methyl-tertbutylether and then dried. The crude peptide was dissolved in water, the aqueous solution was extracted with ethylacetate and then treated with ion exchange resin (IRA 93, acetate form). The ion exchanger was removed by filtration, washed with water and the aqueous solution was lyophillized. The crude peptide now obtained as acetate was purified by chromatography on Sephadex® LH 20 with 10 % aqueous acetic acid. The fractions which contain the pure peptide were combined and lyophillized.
MS(FAB): 992.6 (M+H).

The following are $IC_{50}$ data for various Examples previously set forth.

| Example No. | $IC_{50}$ [M] |
| --- | --- |
| 1 | $4.6 \times 10^{-6}$ |
| 3 | $2.1 \times 10^{-6}$ |
| 4 | $1.2 \times 10^{-5}$ |
| 5 | $2.4 \times 10^{-5}$ |
| 6 | $2.5 \times 10^{-7}$ |
| 7 | $3.7 \times 10^{-5}$ |
| 8 | $1.9 \times 10^{-7}$ |
| 9 | $4.6 \times 10^{-5}$ |
| 13 | $6.0 \times 10^{-5}$ |
| 19 | $3.4 \times 10^{-8}$ |
| 23 | $4.8 \times 10^{-7}$ |
| 24 | $1.1 \times 10^{-8}$ |
| 27 | $2.5 \times 10^{-5}$ |
| 29 | $3.7 \times 10^{-7}$ |
| 38 | $6.0 \times 10^{-5}$ |
| 39 | $1.7 \times 10^{-6}$ |
| 44 | $3.9 \times 10^{-7}$ |
| 45 | $4.8 \times 10^{-7}$ |
| 47 | $1.7 \times 10^{-7}$ |
| 48 | $9.5 \times 10^{-8}$ |
| 54 | $8.9 \times 10^{-6}$ |
| 56 | $8.0 \times 10^{-7}$ |
| 57 | $6.2 \times 10^{-8}$ |
| 58 | $2.6 \times 10^{-5}$ |
| 59 | $5.4 \times 10^{-9}$ |
| 60 | $4.2 \times 10^{-9}$ |
| 64 | $6.8 \times 10^{-9}$ |
| 67 | $6.4 \times 10^{-8}$ |
| 72 | $1.8 \times 10^{-8}$ |
| 73 | $3.0 \times 10^{-8}$ |
| 74 | $4.8 \times 10^{-8}$ |
| 75 | $3.0 \times 10^{-8}$ |
| 76 | $3.2 \times 10^{-7}$ |
| 77 | $7.0 \times 10^{-8}$ |
| 78 | $2.5 \times 10^{-7}$ |
| 79 | $3.5 \times 10^{-8}$ |
| 159 | $7.8 \times 10^{-8}$ |
| 162 | $7.2 \times 10^{-7}$ |
| 165 | $3.0 \times 10^{-8}$ |
| 166 | $4.6 \times 10^{-8}$ |
| 167 | $2.8 \times 10^{-7}$ |
| 168 | $3.2 \times 10^{-7}$ |
| 169 | $2.0 \times 10^{-7}$ |
| 170 | $6.8 \times 10^{-6}$ |
| 171 | $5.0 \times 10^{-5}$ |
| 172 | $1.8 \times 10^{-6}$ |
| 173 | $2.6 \times 10^{-5}$ |
| 174 | $1.3 \times 10^{-8}$ |
| 175 | $1.7 \times 10^{-8}$ |
| 176 | $3.6 \times 10^{-8}$ |
| 177 | $1.1 \times 10^{-7}$ |
| 178 | $1.3 \times 10^{-7}$ |
| 179 | $1.8 \times 10^{-7}$ |
| 180 | $1.8 \times 10^{-7}$ |
| 181 | $2.4 \times 10^{-7}$ |
| 182 | $2.9 \times 10^{-7}$ |
| 183 | $8.0 \times 10^{-6}$ |
| 184 | $2.3 \times 10^{-8}$ |
| 185 | $4.4 \times 10^{-6}$ |
| 186 | $3.2 \times 10^{-7}$ |
| 188 | $3.4 \times 10^{-7}$ |
| 189 | $1.6 \times 10^{-8}$ |
| 190 | $6.6 \times 10^{-9}$ |
| 191 | $1.2 \times 10^{-8}$ |
| 192 | $1.5 \times 10^{-7}$ |
| 193 | $8.9 \times 10^{-8}$ |
| 194 | $4.2 \times 10^{-8}$ |

In the following Examples 196–198, the amino acid derivatives below were used:

Fmoc-Arg(Mtr)-OH, Boc-(D)-Arg-OH, Fmoc-Arg(Pmc)-OH, Fmoc-Hyp-OH, Fmoc-Pro-OObt, Fmoc-Gly-OObt, Fmoc-Phe-OObt, Fmoc-Ser(tBu)-OObt, Fmoc-(D)-Phe-OH, Fmoc-Gln-OH, Fmoc-Aoc-OH, Fmoc-Thia-OH, Fmoc-Opr-OH, Fmoc-(D)-Asn-OH, Fmoc-β-Ala-OH, Fmoc-Oic-OH.

EXAMPLE 196

H-(D)-Arg-Arg-Pro-Hyp-Gly-Phe-Ser-(D)-Phe-Oic-Arg-OH was synthesized stepwise using a peptide synthesizer model 430 A from Applied Biosystems by the Fmoc method on a p-benzyloxybenzyl alcohol resin from Novabiochem (loading about 0.5 mmol/g of resin) esterified with Fmoc-Arg(Mtr)-OH. 1 g of the resin was employed and the synthesis was carried out with the aid of a synthesis program modified for the Fmoc method.

In each case 1 mmol of the amino acid derivative having a free carboxyl group together with 0.95 mmol of HOObt was weighed into the cartridges of the synthesizer. The preactivation of these amino acids was carried out directly in the cartridges by dissolving in 4 ml of DMF and adding 2 ml of a 0.55 ml solution of diisopropyl-carbodiimide in DMF.

The HOObt esters of the other amino acids were dissolved in 6 ml of NMP and then similarly coupled to the resin previously deblocked using 20% piperidine in DMF, like the amino acids preactivated in situ. After completion of the synthesis, the peptide was split off from the resin using thioanisole and ethanedithiol as cation entrainers, with simultaneous removal of the side chain protective groups using trifluoroacetic acid. The residue obtained after stripping off the trifluoroacetic acid was repeatedly digested with ethyl acetate and centrifuged. The residue which remained was chromatographed on ®Sephadex LH 20 using 10% strength acetic acid. The fractions containing the pure peptide were combined and freeze-dried.

MS(FAB): 1292.4 (M+H)

Examples 197–198 were prepared analogously to Example 196.

EXAMPLE 197

H-(D)-Arg-Arg-Pro-Hyp-Gly-Thia-Ser-(D)-Phe-Oic-Arg-OH
MS(FAB)=1292.7

EXAMPLE 198

H-(D)-Arg-Arg-Pro-Pro-Gly-Phe-Ser-(D)-(p-Cl)Phe-Oic-Arg-OH
MS(FAB)=1305.0

In the following Examples 199–201, the amino acid derivatives below were used:

Fmoc-Arg(Mtr)-OH, Boc-(D)-Arg-OH, Fmoc-Arg(Pmc)-OH, Fmoc-Hyp-OH, Fmoc-Pro-OObt, Fmoc-Gly-OObt, Fmoc-Phe-OObt, Fmoc-Ser(tBu)-OObt, Fmoc-(D)-Tic-OH, Fmoc-Gln-OH, Fmoc-Aoc-OH, Fmoc-Thia-OH, Fmoc-Opr-OH, Fmoc-(D)-Asn-OH, Fmoc-β-Ala-OH, Fmoc-Oic-OH.

EXAMPLE 199

H-(D)-Arg-Arg-Pro-Hyp-Gly-Leu-Ser-(D)-Tic-Oic-Arg-OH was synthesized stepwise using a model 430 A peptide synthesizer from Applied Biosystems and using the Fmoc method on a p-benzyloxybenzyl alcohol-resin esterified with Fmoc-Arg(Mtr)-OH from Novabiochem (loading about 0.5 mmol/g of resin). 1 g of the resin was employed, and the synthesis was carried out using a synthesis program modified for the Fmoc method.

In each case, 1 mmol of the amino acid derivatives with free carboxyl group were weighed together with 0.95 mmol of HOObt into the synthesizer cartridges. These amino acids were preactivated directly in the cartridges by dissolving in 4 ml of DMF and adding 2 ml of a 0.55 mol/l solution of diisopropylcarbodiimide in DMF. The HOObt esters of the other amino acids were dissolved in 6 ml of NMP and then coupled just like the in situ preactivated amino acids to the resin which had previously been deblocked with 2% piperidine in DMF. After the synthesis was complete, the peptide was cleaved off the resin with simultaneous removal of the side-chain protective groups with trifluoroacetic acid using thioanisole and ethanedithiol as cation traps. The residue obtained after stripping off the trifluoroacetic acid was digested several times with ethyl acetate and centrifuged. The remaining residue was chromatographed on ®Sephadex LH 20 with 10% strength acetic acid. The fractions containing the pure peptide were combined and freeze-dried.

MS(FAS): 1264 (M+H)

Examples 200–201 were prepared analogously to Example 199.

EXAMPLE 200

H-(D)-Arg-Arg-Pro-Hyp-Gly-Cha-Ser-(D)-Tic-Oic-Arg-OH
MS (FAB): 1304 (M+H)

EXAMPLE 201

H-(D)-Arg-Arg-Pro-Hyp-Gly-Tbg-Ser-(D)-Tic-Oic-Arg-OH
MS (FAB): 1264 (M+H)

It will be apparent to those skilled in the art that various modifications and variations can be made in the present invention without deviating from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims or their equivalents.

What is claimed is:

1. A peptide of the formula I $$A\text{-}B\text{-}C\text{-}E\text{-}F\text{-}K\text{-}P\text{-}G\text{-}M\text{-}F \qquad (I)$$

in which
A is $a_1$, $a_2$, or $a_3$, wherein
  $a_1$) is
    hydrogen,
    $(C_1\text{–}C_8)$-alkyl,
    $(C_1\text{–}C_8)$-alkanoyl,
    $(C_1\text{–}C_8)$-alkoxycarbonyl or
    $(C_1\text{–}C_8$-alkylsulfonyl,
    in which in each case 1, 2 or 3 hydrogen atoms are optionally replaced by 1, 2 or 3 identical or different radicals selected from
      carboxyl,
      amino,
      $(C_1\text{–}C_4)$-alkyl,
      $(C_1\text{–}C_4)$-alkylamino,
      hydroxyl, ($C_1$–$C_4$)-alkoxy,
halogen,
di-($C_1$–$C_4$)-alkylamino,
carbamoyl,
sulfamoyl,
($C_1$–$C_4$)-alkoxycarbonyl,
($C_6$–$C_{12}$)-aryl, and
($C_6$–$C_{12}$)-aryl-($C_1$–$C_5$)-alkyl,
or in which in each case 1 hydrogen atom is optionally replaced by a radical selected from
($C_3$–$C_8$)-cycloalkyl,
($C_1$–$C_4$)-alkylsulfonyl,
($C_1$–$C_4$)-alkylsulfinyl,
($C_6$–$C_{12}$)-aryl-($C_1$–$C_4$)-alkylsulfonyl
($C_6$–$C_{12}$)-aryl-($C_1$–$C_4$)-alkylsulfinyl,
($C_6$–$C_{12}$)-aryloxy,
($C_3$–$C_9$)-heteroaryl and
($C_3$–$C_9$)-heteroaryloxy and
1 or 2 hydrogen atoms are replaced by 1 or 2 identical or different radicals selected from
carboxyl,
amino,
($C_1$–$C_4$)-alkylamino,
hydroxyl,
($C_1$–$C_4$)-alkoxy,
halogen,
di-($C_1$–$C_4$)-alkylamino,
carbamoyl,
sulfamoyl,
($C_1$–$C_4$)-alkoxycarbonyl,
($C_6$–$C_{12}$)-aryl and
($C_6$–$C_{12}$)-aryl-($C_1$–$C_5$)-alkyl, or $a_2$) is ($C_3$–$C_8$)-cycloalkyl,
carbamoyl, which may be optionally substituted on the nitrogen by ($C_1$–$C_6$)-alkyl or ($C_6$–$C_{12}$)-aryl,
($C_6$–$C_{12}$)-aryl,
($C_7$–$C_{18}$)-aryloyl,
($C_6$–$C_{12}$)-arylsulfonyl,
($C_3$–$C_9$)-heteroaryl or
($C_3$–$C_9$)-heteroaryloyl,
wherein for the radicals defined under $a_1$) and $a_2$) in each case aryl, heteroaryl, aryloyl, arylsulfonyl, and heteroaryloyl is optionally substituted by 1, 2, 3 or 4 identical or different radicals selected from
carboxyl,
amino,
nitro,
($C_1$–$C_4$)-alkylamino,
hydroxyl,
($C_1$–$C_4$)-alkyl
($C_1$–$C_4$)-alkoxy,
halogen,
cyano,
di-($C_1$–$C_4$)-alkylamino,
carbamoyl,
sulfamoyl and
($C_1$–$C_4$)-alkoxycarbonyl, $a_3$) is a radical of the formula II

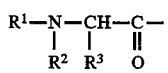  (II)

$R^1$ is defined as A under $a_1$) or $a_2$);
$R^2$ is hydrogen or methyl,
$R^3$ is hydrogen or ($C_1$–$C_6$)-alkyl which is optionally monosubstituted by
amino,
substituted amino,
hydroxyl,
carboxyl,
carbamoyl,
guanidino,
substituted guanidino,
ureido,
mercapto,
methylmercapto,
phenyl,
4-chlorophenyl,
4-fluorophenyl,
4-nitrophenyl,
4-methoxyphenyl,
4-hydroxyphenyl,
phthalimido,
4-imidazolyl,
3-indolyl,
2-thienyl,
3-thienyl,
2-pyridyl,
3-pyridyl or
cyclohexyl,
wherein substituted amino is a compound of the formula —NH—A— and substituted guanidino is a compound of the formula —NH—C(NH)—NH—A, in which A is defined under $a_1$) or $a_2$);

B is a basic amino acid in the L- or D-configuration, which may be substituted in the side chain;

C is a compound of the formula IIIa or IIIb

  (IIIa)

  (IIIb)

in which

G' independently of one another is a radical of the formula IV

  (IV)

in which $R^4$ and $R^5$ together with the atoms carrying them form a heterocyclic monocyclic, bicyclic or tricyclic ring system having 2 to 15 carbon atoms, and n is 2 to 8;

E is a radical of an aromatic amino acid;

F is a radical of a neutral, acidic or basic, aliphatic or aromatic amino acid which may be substituted in the side chain, or is a direct bond;

P is a radical of the formula V ((D)-Tic);

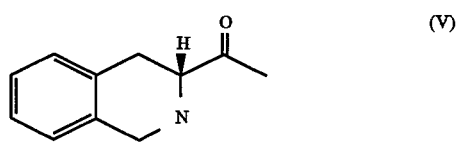  (V)

G is as defined above for G' or is a direct bond;

F' is a radical of a neutral, acidic or basic aliphatic or aromatic amino acid which may be substituted in the side chain, is a radical —NH—($CH_2$)$_n$—, with n=2 to 8, or is a direct bond;

I is —OH, —$NH_2$ or —$NHC_2H_5$, wherein I is not directly bonded to P;

K is a radical —NH—($CH_2$)$_x$—CO— with x=1–4 or is a direct bond; and

M is as defined for F,
or a physiologically tolerable salt of said peptide.

2. A peptide of the formula I or salt as claimed in claim 1 in which

B is Arg, Lys, Orn, 2,4-diamino-butyroyl or an L-homoarginine radical, wherein in each case the amino or guanidino group of the side chain may be substituted by A as defined under $a_1$) or $a_2$);

C is a compound of the formula IIIa

in which
each G' independently is a radical of the formula IV $$\begin{array}{ccc} R^4 & R^5 & O \\ | & | & \| \\ -N-CH-C- \end{array} \quad \text{(IV)}$$

in which
$R^4$ and $R^5$ together with the atoms carrying them form a heterocyclic monocyclic, bicyclic or tricyclic ring system having 2 to 15 carbon atoms;

E is a radical of an aromatic amino acid in the L- or D-configuration, which contains 6 to 14 carbon atoms in the aryl moiety as ring members, which is optionally substituted by halogen in the 2-, 3- or 4-position, tyrosine, O-methyltyrosine, 2-thienylalanine, 2-pyridylalanine or naphthylalanine;

F is a direct bond or a radical of a neutral aliphatic or aromatic amino acid which may be substituted in the side chain;

F' is a radical of a basic amino acid in the L- or D-configuration, wherein the guanidino group or amino group of the side chain may be replaced by A as defined under $a_1$) or $a_2$), or is a radical —NH—$(CH_2)_n$— with n=2 to 8;

K is a radical —NH—$(CH_2)_x$—CO— with x=1–4 or is a direct bond; and

M is Phe, Thia or a direct bond.

3. A peptide of the formula I or salt as claimed in claim 2 in which

F' is Arg or Lys, wherein the guanidino group or amino group of the side chain may be replaced by A as defined under $a_1$) or $a_2$), or is a radical —NH—$(CH_2)_n$— with n=2 to 8; and G' is a heterocyclic monocyclic or bicyclic ring system having 3 or 4 carbon atoms if said ring system is monocyclic or having 7 to 9 carbon atoms if said ring system is bicyclic.

4. A peptide of the formula I or salt as claimed in claim 1 in which

B is Arg, Orn or Lys, wherein the guanidino group or the amino group of the side chain is unsubstituted or is substituted by ($C_1$–$C_8$)-alkanoyl, ($C_7$–$C_{13}$)-aryloyl, ($C_3$–$C_9$)-heteroaryloyl, ($C_1$–$C_8$)-alkylsulfonyl or ($C_6$–$C_{12}$)-arylsulfonyl, wherein in each case the aryloyl, arylsulfonyl and heteroaryloyl radicals are optionally substituted by 1, 2, 3 or 4 identical or different radicals selected from
carboxyl,
amino,
nitro,
($C_1$–$C_4$)-alkylamino,
hydroxyl,
($C_1$–$C_4$)-alkyl,
($C_1$–$C_4$)-alkoxy,
halogen,
cyano,
di-($C_1$–$C_4$)-alkylamino,
carbamoyl,
sulfamoyl and
($C_1$–$C_4$)-alkoxycarbonyl;

E is phenylalanine, 2-chlorophenylalanine, 3-chlorophenylalanine, 4-chlorophenylalanine, 2-fluoro-phenylalanine, 3-fluorophenylalanine, 4-fluorophenylalanine, tyrosine, O-methyltyrosine or β-(2-thienyl)alanine;

F is Ser, hSer, Leu, Val, Nle, Thr, Gln, Trp, (D)Asn, Opr, (D)Ser, (D)Gln or a direct bond;

F' is Arg, wherein the guanidino group of the side chain may be replaced by A as defined under $a_1$) or $a_2$), or is a radical —NH—$(CH_2)_n$— with n=2 to 8;

K is a radical —NH—$(CH_2)_x$—CO— with x=1 or is a direct bond;

M is a direct bond; and

I is OH or $NH_2$.

5. A peptide of the formula I or salt as claimed in claim 1 in which

A is hydrogen, (D)- or (L)-H-Arg, (D)- or (L)-H-Lys or (D)- or (L)-H-Orn;

B is Arg, Orn or Lys, wherein the guanidino group or the amino group of the side chain is optionally substituted by ($C_1$–$C_8$)-alkanoyl, ($C_7$–$C_{13}$)-aryloyl, ($C_3$–$C_9$)-heteroaryloyl, ($C_1$–$C_{12}$)-alkylsulfonyl or ($C_6$–$C_{12}$)-arylsulfonyl, wherein the aryloyl, arylsulfonyl and heteroaryloyl radicals are optionally substituted with 1, 2, 3 or 4 identical or different radicals selected from the group consisting of methyl, methoxy and halogen;

C is Pro-Pro-Gly, Hyp-Pro-Gly or Pro-Hyp-Gly;

E is Phe or Thia;

F is Ser, hSer, Leu, Val, Nle, Thr, Gln, Trp, (D)Asn, Opr, (D)Ser, (D)Gln or a direct bond;

K is a radical —NH—$(CH_2)_x$—CO— with x=1 or is a direct bond;

M is a direct bond;

G is a radical of the formula IV

in which
$R^4$ and $R^5$ together with the atoms carrying them form a heterocyclic monocyclic, bicyclic or tricyclic ring system having 2 to 15 carbon atoms;

F' is Arg; and

I is OH.

6. A peptide of the formula I or salt as claimed in claim 1 in which

A is hydrogen, (D)- or (L)-H-Arg, (D)- or (L)-H-Lys or (D)- or (L)-H-Orn;

B is Arg, Orn or Lys, wherein the guanidino group or the amino group of the side chain is optionally substituted by ($C_1$–$C_8$)-alkanoyl, ($C_7$–$C_{13}$)-aryloyl, ($C_3$–$C_9$)-heteroaryloyl, ($C_1$–$C_8$)-alkylsulfonyl or ($C_6$–$C_{12}$)-arylsulfonyl, wherein the aryloyl, arylsulfonyl and heteroaryloyl radicals are optionally substituted with 1, 2, 3 or 4 identical or different radicals selected from the group consisting of methyl, methoxy and halogen;

C is Pro-Pro-Gly, Hyp-Pro-Gly or Pro-Hyp-Gly;

E is Phe or Thia;

F is Ser or a direct bond;

K is a direct bond or —NH—(CH$_2$)$_x$—CO— with x=1–4, wherein when F is serine, K is a direct bond, and when K is —NH—(CH$_2$)$_x$—CO—, F is a direct bond;

M is a direct bond;

G is a radical of the formula IV

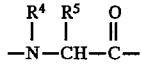

in which

R$^4$ and R$^5$ together with the atoms carrying them form a heterocyclic monocyclic, bicyclic or tricyclic ring system having 2 to 15 carbon atoms;

F' is Arg; and

I is OH.

7. A peptide of the formula I or salt as claimed in claim 1 in which

A is hydrogen, (D)- or (L)-H-Arg, (D)- or (L)-H-Lys or (D)- or (L)-H-Orn;

B is Arg, Orn or Lys, wherein the guanidino group or the amino group of the side chain is optionally substituted by (C$_1$–C$_8$)-alkanoyl, (C$_7$–C$_{13}$)-aryloyl, (C$_3$–C$_9$)-heteroaryloyl, (C$_1$–C$_8$)-alkylsulfonyl or (C$_6$–C$_{12}$)-arylsulfonyl, wherein the aryloyl, arylsulfonyl and heteroaryloyl radicals are optionally substituted with 1, 2, 3 or 4 identical or different radicals selected from the group consisting of methyl, methoxy and halogen;

C is Pro-Pro-Gly, Hyp-Pro-Gly or Pro-Hyp-Gly;

E is Phe or Thia;

F is Cys

K is a radical —NH—(CH$_2$)$_x$—CO— with x=1 or is a direct bond;

M is a direct bond;

G is a radical of the formula IV

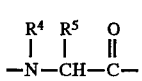

in which

R$^4$ and R$^5$ together with the atoms carrying them form a heterocyclic monocyclic, bicyclic or tricyclic ring system having 2 to 15 carbon atoms, F' is Arg; and I is OH.

8. A peptide of the formula I or salt as claimed in claim 5, in which

G is a radical selected from the group consisting of pyrrolidine (A), piperidine (B), tetra-hydroisoquinoline (C), cis- and trans-decahydroisoquinoline (D), cis-endo-, cis-exo, and trans-octahydroindole (E), cis-endo-, cis-exo-, and trans-octa-hydrocyclopentano[b] pyrrole (F), and hydroxyproline (V).

9. A peptide of the formula I or salt as claimed in claim 6, in which

G is a radical selected from the group consisting of pyrrolidine (A), piperidine (B), tetra-hydroisoquinoline (C), cis- and trans-decahydroisoquinoline (D), cis-endo-, cis-exo, and trans-octahydroindole (E), cis-endo-, cis-exo-, and trans-octa-hydrocyclopentano[b] pyrrole (F), and hydroxyproline (V).

10. A peptide of the formula I or salt as claimed in claim 1, in which

A is hydrogen or D-Arg,

B is Arg, Arg(NO$_2$) or Arg(Tos),

C is Hyp-Pro-Gly, Pro-Hyp-Gly, or Pro-Pro-Gly

E is Thia or Phe,

F is Ser,

K is a direct bond,

G is Aoc, Tic or Oic,

M is a direct bond,

F' is Arg, and

I is OH.

11. A peptide of the formula I or salt as claimed in claim 1, in which

A is hydrogen or D-Arg,

B is Arg or Arg(Tos),

C is Pro-Hyp-Gly,

E is Thia,

F is Ser,

K is a direct bond,

G is Aoc or Oic,

M is a direct bond,

F' is Arg, and

I is OH.

12. A peptide of the formula

H-D-Arg-Arg-Hyp-Pro-Gly-Phe-Ser-D-Tic-Oic-Arg-OH,
H-D-Arg-Arg-Pro-Pro-Gly-Phe-Ser-D-Tic-Oic-Arg-OH,
H-D-Arg-Arg-Hyp-Pro-Gly-Thia-Ser-D-Tic-Aoc-Arg-OH,
H-D-Arg-Arg-Pro-Hyp-Gly-Thia-Ser-D-Tic-Aoc-Arg-OH,
H-D-Arg-Arg-Pro-Hyp-Gly-Thia-Ser-D-Tic-Tic-Arg-OH,
H-D-Arg-Arg-Pro-Hyp-Gly-Thia-Ser-D-Tic-Aoc-Arg-OH,
H-D-Arg-Arg-Pro-Pro-Gly-Thia-Ser-D-Tic-Oic-Arg-OH,
H-D-Arg-Arg-Pro-Hyp-Gly-Phe-Ser-D-Tic-Oic-Arg-OH,
H-D-Arg-Arg(NO$_2$)-Pro-Hyp-Gly-Phe-Ser-D-Tic-Aoc-Arg-OH, or
H-Arg(Tos)-Pro-Hyp-Gly-Thia-Ser-D-Tic-Oic-Arg-OH,
or a physiologically tolerable salt of said peptide.

13. A peptide of the formula

H-D-Arg-Arg-Pro-Hyp-Gly-Thia-Ser-D-Tic-Aoc-Arg-OH,
H-D-Arg-Arg-Pro-Hyp-Gly-Thia-Ser-D-Tic-Oic-Arg-OH, or
H-Arg (Tos)-Pro-Hyp-Gly-Thia-Ser-D-Tic-Oic-Arg-OH,
or a physiologically tolerable salt of said peptide.

14. A peptide of the formula

H-D-Arg-Arg-Pro-Hyp-Gly-Thia-Ser-D-Tic-Oic-Arg-OH
or a physiologically tolerable salt of said peptide.

15. A peptide of the formula I $$A\text{-}B\text{-}C\text{-}E\text{-}F\text{-}K\text{-}P\text{-}G\text{-}M\text{-}F'\text{-}I \quad (I)$$

in which

A a$_1$) is hydrogen,
(C$_1$–C$_8$)-alkyl,
(C$_1$–C$_8$)-alkanoyl,
(C$_1$–C$_8$)-alkoxycarbonyl or
(C$_1$–C$_8$)-alkylsulfonyl,
in which in each case 1, 2 or 3 hydrogen atoms are optionally replaced by 1, 2 or identical or different radicals selected from
carboxyl,
amino,
(C$_1$–C$_4$)-alkyl,
(C$_1$–C$_4$)-alkylamino,
hydroxyl,
(C$_1$–C$_4$)-alkoxy,
halogen,
di-(C$_1$–C$_4$)-alkylamino, carbamoyl,
sulfamoyl,
($C_1$–$C_4$)-alkoxycarbonyl,
($C_6$–$C_{12}$)-aryl, and
($C_6$–$C_{12}$)-aryl-($C_1$–$C_5$)-alkyl,
or in which in each case 1 hydrogen atom is optionally replaced by a radical selected from
($C_3$–$C_8$)-cycloalkyl,
($C_1$–$C_4$)-alkylsulfonyl,
($C_1$–$C_4$)-alkylsulfinyl,
($C_6$–$C_{12}$)-aryl-($C_1$–$C_4$)-alkylsulfonyl
($C_6$–$C_{12}$)-aryl-($C_1$–$C_4$)-alkylsulfinyl,
($C_6$–$C_{12}$)-aryloxy,
($C_3$–$C_9$)-heteroaryl and
($C_3$–$C_9$)-heteroaryloxy and
1 or 2 hydrogen atoms are replaced by 1 or 2 identical or different radicals selected from
carboxyl,
amino,
($C_1$–$C_4$)-alkylamino,
hydroxyl,
($C_1$–$C_4$)-alkoxy,
halogen,
di-($C_{1-4}$)-alkylamino,
carbamoyl,
sulfamoyl,
($C_1$–$C_4$)-alkoxycarbonyl,
($C_6$–$C_{12}$)-aryl, and
($C_6$–$C_{12}$)-aryl-($C_1$–$C_5$)-alkyl,
$a_2$) is ($C_3$–$C_8$)-cycloalkyl,
carbamoyl, which may be optionally substituted on the nitrogen by ($C_1$–$C_6$)-alkyl or ($C_6$–$C_{12}$)-aryl,
($C_6$–$C_{12}$)-aryl,
($C_7$–$C_{18}$)-aryloyl,
($C_6$–$C_{12}$)-arylsulfonyl,
($C_3$–$C_9$)-heteroaryl or
($C_3$–$C_9$)-heteroaryloyl,
wherein for the radicals defined under $a_1$) and $a_2$) in each case aryl, heteroaryl, aryloyl, arylsulfonyl and heteroaryloyl is optionally substituted by 1, 2, 3 or 4 identical or different radicals selected from
carboxyl,
amino,
nitro,
($C_1$–$C_4$)-alkylamino,
hydroxyl,
($C_1$–$C_4$)-alkyl,
($C_1$–$C_4$)-alkoxy,
halogen,
cyano,
di-($C_1$–$C_4$)-alkylamino,
carbamoyl,
sulfamoyl and
($C_1$–$C_4$)-alkoxycarbonyl, or
$a_3$) is a radical of the formula II

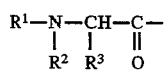  (II)

$R^1$ is defined as A under $a_1$) or $a_2$),
$R^2$ is hydrogen or methyl,
$R^3$ is hydrogen or ($C_1$–$C_6$)-alkyl which is optionally monosubstituted by
amino,
substituted amino,
hydroxyl,
carboxyl,
carbamoyl,
guanidino,
substituted guanidino,
ureido,
mercapto,
methylmercapto,
phenyl,
4-chlorophenyl,
4-fluorophenyl,
4-nitrophenyl,
4-methoxyphenyl,
4-hydroxyphenyl,
phthalimido,
4-imidazolyl,
3-indolyl,
2-thienyl,
3-thienyl,
2-pyridyl,
3-pyridyl or
cyclohexyl,
wherein substituted amino is a compound of the formula —NH—A— and substituted guanidino is a compound of the formula —NH—C(NH)—NH—A, in which A is defined under $a_1$) or $a_2$);

B is a basic amino acid in the L- or D-configuration, which may be substituted in the side chain;

C is a compound of the formula IIIa or IIIb

  (IIIa)

  (IIIb)

in which
each G' independently is a radical of the formula IV

  (IV)

in which
$R^4$ and $R^5$ together with the atoms carrying them form a heterocyclic monocyclic, bicyclic or tricyclic ring system having 2 to 15 carbon atoms, and n is 2 to 8;

E is a radical of an aromatic amino acid;

F is a radical of a neutral, acidic or basic, aliphatic or aromatic amino acid which may be substituted in the side chain, or is a direct bond;

P is D-phenylalanine ((D)-Phe) which may be optionally substituted in the phenyl moiety;

G is a radical of the formula IV in which $R_4$ and $R_5$ together with the atoms carrying them form a heterocyclic bicyclic or tricyclic ring system having 7 to 15 carbon atoms;

F' is a radical of a neutral, acidic, or basic aliphatic or aromatic amino acid which may be substituted in the side chain, or is a radical —NH—$(CH_2)_n$—, with n=2 to 8, or is a direct bond;

I is —OH, —$NH_2$ or —$NHC_2H_5$;

K is a radical —NH—$(CH_2)_x$—CO— with x=1–4 or is a direct bond, and

M is as defined for F,
or a physiologically tolerable salt thereof.

16. A peptide of the formula I or salt as claimed in claim 15 in which

B is Arg, Lys, Orn, 2,4-diaminobutyroyl or an L-homoarginine radical, wherein in each case the amino or guanidino group of the side chain may be substituted by A as defined under $a_1$) or $a_2$);

C is a compound of the formula IIIa

in which
each G' independently is a radical of the formula IV

in which
R⁴ and Rˢ together with the atoms carrying them form a heterocyclic monocyclic, bicyclic or tricyclic ring system having 2 to 15 carbon atoms;

E is a radical of an aromatic amino acid in the L- or D-configuration, which contains 6 to 14 carbon atoms in the aryl moiety as ring members, which is optionally substituted by halogen in the 2-, 3- or 4-position, tyrosine, O-methyltyrosine, 2-thienylalanine, 2-pyridylalanine or naphthylalanine;

P is D-Phe which is optionally substituted in the phenyl moiety by halogen or $(C_1-C_4)$-alkoxy;

F' is a radical of a basic amino acid in the L- or D-configuration, wherein the guanidino group or amino group of the side chain may be replaced by A as defined under $a_1$) or $a_2$), or is a radical —NH—$(CH_2)_n$— with n=2 to 8;

G is a radical of the formula IV in which $R^4$ and $R^5$ together with the atoms carrying them form a heterocyclic bicyclic ring system having from 7 to 9 carbon atoms;

F is a direct bond or a radical of a neutral aliphatic or aromatic amino acid which may be substituted in the side chain; and K is a direct bond.

17. A peptide of the formula I or salt as claimed in claim 16 in which
F' is Arg or Lys, wherein the guanidino group or amino group of the side chain may be replaced by A as defined under $a_1$) or $a_2$), or is a radical —NH—$(CH_2)_n$— with n=2 to 8;
G is a heterocyclic radical selected from octahydroindole (E), octahydrocyclopenta[b]pyrrole (F), decahydrocyclohepta[b]pyrrole (N), octahydroisoindole (O), and decahydroisoquinoline (D); and
G' is a heterocyclic monocyclic or bicyclic ring system having 4 or 5 carbon atoms if said ring system is monocyclic or having 7 to 9 carbon atoms if said ring system is bicyclic.

18. A peptide of the formula I or salt as claimed in claim 15 in which
B is Arg, Orn or Lys, wherein the guanidino group or the amino group of the side chain is unsubstituted or is substituted by $(C_1-C_8)$-alkanoyl, $(C_7-C_{18})$-aryloyl, $(C_3-C_9)$-heteroaryloyl, $(C_1-C_8)$-alkylsulfonyl or $(C_6-C_{12})$-arylsulfonyl, wherein in each case the aryloyl, arylsulfonyl and heteroaryloyl radicals are optionally substituted by 1, 2, 3 or 4 identical or different radicals selected from
carboxyl,
amino,
nitro,
$(C_1-C_4)$-alkylamino,
hydroxyl,
$(C_1-C_4)$-alkyl,
$(C_1-C_4)$-alkoxy,
halogen,
cyano,
di-$(C_1-C_4)$-alkylamino,
carbamoyl,
sulfamoyl and
$(C_1-C_4)$-alkoxy-carbonyl;

C is a compound of the formula IIIa

in which
each G' independently is a radical of the formula IV

in which $R^4$ and $R^5$ together with the atoms carrying them form a heterocyclic monocyclic, bicyclic or tricyclic ring system having 2 to 15 carbon atoms;

E is phenylalanine, 2-chlorophenylalanine, 3-chlorophenylalanine, 4-chlorophenylalanine, 2-fluorophenylalanine, 3-fluorophenylalanine, 4-fluorophenylalanine, tyrosine, O-methyltyrosine or β-(2-thienyl)-alanine;

F is Ser, hSer, Lys, Leu, Val, Nle, Ile, D-Ser, D-Gln, or Thr;

F' is Arg;

P is D-Phe which is optionally substituted by fluorine, chlorine, bromine or methoxy;

K is a direct bond;

M is a direct bond; and

I is —OH, —NH₂ or —NHC₂H₅.

19. A peptide of the formula I or salt as claimed in claim 15 in which
A is hydrogen, (D)- or (L)-H-Arg, (D)- or (L)-H-Lys or (D)- or (L)-H-Orn;
B is Arg, Orn or Lys, wherein the guanidino group or the amino group of the side chain is optionally substituted by $(C_1-C_8)$-alkanoyl, $(C_7-C_{13})$-aryloyl, $(C_3-C_9)$-heteroaryloyl, $(C_1-C_8)$-alkylsulfonyl or $(C_6-C_{12})$-arylsulfonyl, wherein the aryloyl, arylsulfonyl and heteroaryloyl radicals are optionally substituted with 1, 2, 3 or 4 identical or different radicals selected from the group consisting of methyl, methoxy and halogen;
C is Pro-Pro-Gly, Hyp-Pro-Gly or Pro-Hyp-Gly;
E is Phe or Thia;
F is Ser;
K is a direct bond;
M is a direct bond;
G is Oic;
F' is Arg; and
I is OH.

20. A peptide of the formula I or salt as claimed in claim 19, in which
G is a heterocyclic radical selected from octahydroindole (E), octahydrocyclopenta[b]pyrrole (F), decahydrocyclohepta[b]pyrrole (N), octahydroisoindole (O), and decahydroisoquinoline (D).

21. A peptide of the formula
H-(D)-Arg-Arg-Pro-Hyp-Gly-Phe-Ser-(D)-Phe-Oic-Arg-OH or a physiologically tolerable salt of said peptide.

22. A peptide of the formula
H-(D)-Arg-Arg-Pro-Hyp-Gly-Thia-Ser-(D)-Phe-Oic-Arg-OH or a physiologically tolerable salt of said peptide.

23. A peptide of the formula
H-(D)-Arg-Arg-Pro-Pro-Gly-Phe-Ser-(D)-(p-Cl)Phe-Oic-Arg-OH or a physiologically tolerable salt of said peptide.

24. A peptide of the formula
H-(D)-Arg-Arg-Pro-Hyp-Gly-Tbg-Ser-(D)-Tic-Oic-Arg-OH or a physiologically tolerable salt of said peptide.

25. A method for the treatment of a pathological state which is mediated, caused or supported by bradykinin and bradykinin-related peptides in a patient, wherein said pathological state is selected from the group consisting of wounds, burns, rashes, erythemas, edemas, angina, arthritis, asthma, allergies, rhinitis, shock, inflammations, low blood pressure, pain, itching, and changed sperm motility, wherein said method comprises administering to said patient an effective amount of the peptide as claimed in claim 1 or a physiologically tolerated salt of said peptide.

26. A method of treating asthma in a human comprising administering to said human an effective amount of the peptide as claimed in claim 1, or a physiologically tolerated salt of said peptide.

27. A pharmaceutical composition for the treatment of a pathological state which is mediated, caused or supported by bradykinin and bradykin-related peptides, wherein said pathological state is selected from the group consisting of wounds, burns, rashes, erythemas, edemas, angina, arthritis, asthma, allergies, rhinitis, shock, inflammations, low blood pressure, pain, itching, and changed sperm motility, wherein said pharmaceutical composition comprises an effective amount of the peptide as claimed in claim 1 or a physiologically tolerated salt of said peptide, and a pharmaceutically acceptable vehicle.

28. A method for the treatment of a pathological state which is mediated, caused or supported by bradykinin and bradykinin-related peptides in a patient, wherein said pathological state is selected from the group consisting of wounds, burns, rashes, erythemas, edemas, angina, arthritis, asthma, allergies, rhinitis, shock, inflammations, low brood pressure, pain, itching, and changed sperm motility, wherein said method comprises administering to said patient an effective amount of the peptide as claimed in claim 15, or a physiologically tolerated salt of said peptide.

29. A method of treating asthma in a human comprising administering to said human an effective amount of the peptide as claimed in claim 15, or a physiologically tolerated salt of said peptide.

30. A pharmaceutical composition for the treatment of a pathological state which mediated, caused or supported by bradykinin and bradykinin-related peptides, wherein said pathological state is selected from the group consisting of wounds, burns, rashes, erythemas, edemas, angina, arthritis, asthma, allergies, rhinitis, shock, inflammations, low blood pressure, pain, itching, and changed sperm motility, wherein said pharmaceutical composition comprises an effective amount of the peptide as claimed in claim 15 or a physiologically tolerated salt of said peptide, and a pharmaceutically acceptable vehicle.

31. A method for the treatment of a pathological state which is mediated, caused or supported by bradykinin and bradykinin-related peptides in a patient, wherein said pathological state is selected from the group consisting of wounds, burns, rashes, erythemas, edemas, tonsillitis, arthritis, asthma, allergies, rhinitis, shock, inflammations, low blood pressure, pain, pruritis, and changed sperm motility, wherein said method comprises administering to said patient an effective amount of the peptide as claimed in claim 24, or a physiologically tolerated salt of said peptide.

32. A method of treating asthma in a human comprising administering to said human an effective amount of the peptide as claimed in claim 24, or a physiologically tolerated salt of said peptide.

33. A pharmaceutical composition for the treatment of a pathological state which is mediated, caused or supported by bradykinin and bradykinin-related peptides, wherein said pathological state is selected from the group consisting of wounds, burns, rashes, erythemas, edemas, tonsillitis, arthritis, asthma, allergies, rhinitis, shock, inflammations, low blood pressure, pain, pruritis, and changed sperm motility, wherein said pharmaceutical composition comprises an effective amount of the peptide as claimed in claim 24 or a physiologically tolerated salt of said peptide, and a pharmaceutically acceptable vehicle.

* * * * *

UNITED STATES PATENT AND TRADEMARK OFFICE

(12)          CERTIFICATE EXTENDING PATENT TERM
UNDER 35 U.S.C. § 156

| | | |
|---|---|---|
| (68) PATENT NO. | : | 5,648,333 |
| (45) ISSUED | : | July 15, 1997 |
| (75) INVENTOR | : | Stephan Henke et al. |
| (73) PATENT OWNER | : | Sanofi-Aventis Deutschland GmbH |
| (95) PRODUCT | : | FIRAZYR® (icatibant acetate) |

This is to certify that an application under 35 U.S.C. § 156 has been filed in the United States Patent and Trademark Office, requesting extension of the term of U.S. Patent No. 5,648,333 based upon the regulatory review of the product FIRAZYR® (icatibant acetate) by the Food and Drug Administration. Since it appears that the requirements of the law have been met, this certificate extends the term of the patent for the period of

(94)          5 years from July 15, 2014, the original expiration date of the patent, subject to the payment of maintenance fees as provided by law, with all rights pertaining thereto as provided by 35 U.S.C. § 156.

I have caused the seal of the United States Patent and Trademark Office to be affixed this 16th day of June 2015.

Michelle K. Lee
Under Secretary of Commerce for Intellectual Property and
    Director of the United States Patent and Trademark Office

UNITED STATES PATENT AND TRADEMARK OFFICE
CERTIFICATE OF CORRECTION

PATENT NO. : 5,648,333
DATED : July 15, 1997
INVENTOR(S) : Stephan HENKE, et al.

It is certified that error appears in the above-indentified patent and that said Letters Patent is hereby corrected as shown below:

Claim 1, column 38, line 50, "A-B-C-E-F-K-P-G-M-F'" should read --A-B-C-E-F-K-P-G-M-F'-I--;

line 59, "($C_1$–$C_8$-alkylsulfonyl," --($C_1$–$C_8$)-alkylsulfonyl,--.

Claim 4, column 42, line 12, "Gin" should read --Gln--.

Claim 12, column 44, line 31, (7th line of claim), "Aoc" should read --Oic--.

Claim 15, column 44, line 58, "1,2 or" should read --1,2 or 3--;

column 45, line 60, "$R^2$is" should read --$R^2$ is--;

line 61, "$R^3$is" should read --$R^3$ is--.

UNITED STATES PATENT AND TRADEMARK OFFICE
CERTIFICATE OF CORRECTION

PATENT NO. : 5,648,333
DATED : July 15, 1997
INVENTOR(S) : Stephan HENKE, et al.

It is certified that error appears in the above-indentified patent and that said Letters Patent is hereby corrected as shown below:

Claim 16, column 47, line 11, "$R^S$" should read --$R^5$--.

Claim 18, column 47, line 55, "$(C_7C_{18})$-aryloyl" should read --$(C_7-C_{13})$-aryloyl--.

Claim 30, column 50, line 6, "which mediated" should read --which is mediated--.

Signed and Sealed this

Seventh Day of July, 1998

Attest:

BRUCE LEHMAN

Attesting Officer

Commissioner of Patents and Trademarks